United States Patent
Lifshitz et al.

(10) Patent No.: US 6,767,913 B2
(45) Date of Patent: Jul. 27, 2004

(54) CRYSTAL FORMS III, IV, V, AND NOVEL AMORPHOUS FORM OF CLOPIDOGREL HYDROGENSULFATE, PROCESSES FOR THEIR PREPARATION, PROCESSES FOR THE PREPARATION OF FORM I, COMPOSITIONS CONTAINING THE NEW FORMS AND METHODS OF ADMINISTERING THE NEW FORMS

(75) Inventors: Revital Lifshitz, Herzlia (IL); Eti Kovalevski-Ishai, Netanya (IL); Shlomit Wizel, Petah Tiqva (IL); Sharon Avhar Maydan, Petach Tikva (IL); Rami Lidor-Hadas, Kfar Saba (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/074,409

(22) Filed: Feb. 12, 2002

(65) Prior Publication Data

US 2003/0114479 A1 Jun. 19, 2003

Related U.S. Application Data

(60) Provisional application No. 60/342,440, filed on Dec. 18, 2001, provisional application No. 60/342,351, filed on Dec. 21, 2001, and provisional application No. 60/348,182, filed on Jan. 11, 2002.

(51) Int. Cl.[7] ........................ A61K 31/44; C07D 471/02
(52) U.S. Cl. ........................................ 514/301; 546/114
(58) Field of Search .......................... 546/114; 514/301

(56) References Cited

U.S. PATENT DOCUMENTS

| | | | |
|---|---|---|---|
| 4,529,596 A | 7/1985 | Aubert et al. | 546/114 |
| 4,847,265 A | 7/1989 | Badore et al. | 514/301 |
| 5,036,156 A | 7/1991 | Bouisset et al. | 546/114 |
| 5,132,435 A | 7/1992 | Bousquet et al. | 549/60 |
| 5,204,469 A | 4/1993 | Descamps et al. | 546/114 |
| 5,576,328 A | 11/1996 | Herbert et al. | 514/301 |
| 6,080,875 A * | 6/2000 | Castro et al. | 546/47 |
| 6,180,793 B1 | 1/2001 | Bakonyi et al. | 546/114 |
| 6,215,005 B1 | 4/2001 | Heymes et al. | 549/74 |
| 6,258,961 B1 | 7/2001 | Bakonyi et al. | 549/77 |
| 6,429,210 B1 * | 8/2002 | Bousquet et al. | 514/301 |
| 6,504,030 B1 * | 1/2003 | Bousquet et al. | 546/114 |

FOREIGN PATENT DOCUMENTS

| | | | |
|---|---|---|---|
| EP | 0 281 459 | 9/1988 | |
| FR | 2769313 | 4/1999 | 546/114 |
| WO | WO 98/39286 | 9/1998 | 546/114 |
| WO | WO 98/39322 | 9/1998 | 546/114 |
| WO | WO 98/51681 | 11/1998 | 546/114 |
| WO | WO 98/51682 | 11/1998 | 546/114 |
| WO | WO 98/51689 | 11/1998 | 546/114 |
| WO | WO 99/18110 | 4/1999 | 546/114 |
| WO | WO 99/65915 | 12/1999 | |
| WO | WO 00/27840 | 5/2000 | 546/114 |
| WO | WO 00/66130 | 11/2000 | 546/114 |
| WO | WO 02/059128 | 8/2002 | 546/114 |

OTHER PUBLICATIONS

Reist et al., "Very Slow Chiral Inversion of Clopidogrel in Rats: A Pharmacokinetic and Mechanistic Investigation," Drug Metabolism and Disposition, vol. 28, No. 12, Sep. 11, 2000, pp. 1405–1410.
Harry G. Brittain (Editor) "Polymorphism in Pharmaceutical Solids" Drugs and the Pharmaceutical Sciences vol. 95, (1999) Marcel Dekker, Inc. New York, New York.

* cited by examiner

*Primary Examiner*—Alan L. Rotman
*Assistant Examiner*—Raymond Covington
(74) *Attorney, Agent, or Firm*—Kenyon & Kenyon

(57) ABSTRACT

The present invention provides new crystalline Forms III, IV and V of clopidogrel hydrogensulfate and the amorphous form of clopidogrel hydrogensulfate, as well as their pharmaceutical compositions, and method of treatments with such compositions. The present invention also provides novel processes for preparation of clopidogrel hydrogensulfate Form I, Form III, Form IV, Form V and the amorphous form. The present invention further provides a novel process where the amorphous form is converted to Form I by contacting Form I with an ether.

90 Claims, 11 Drawing Sheets

XRD DIFFRACTOGRAM OF CLOPIDOGREL HYDROGENSULFATE FORM III

DSC THERMOGRAM OF CLOPIDOGREL HYDROGENSULFATE FORM III

FIG. 3 FTIR SPECTRUM OF CLOPIDOGREL HYDROGENSULFATE FORM III

FIG. 5 FTIR SPECTRUM OF CLOPIDOGREL HYDROGENSULFATE AMORPHOUS FORM

ND NOVEL
CRYSTAL FORMS III, IV, V, AND NOVEL AMORPHOUS FORM OF CLOPIDOGREL HYDROGENSULFATE, PROCESSES FOR THEIR PREPARATION, PROCESSES FOR THE PREPARATION OF FORM I, COMPOSITIONS CONTAINING THE NEW FORMS AND METHODS OF ADMINISTERING THE NEW FORMS

CROSS REFERENCE

This Application claims priority to provisional Appl. No. 60/342,440 filed on Dec. 18, 2001, provisional Appl. No. 60/342,351 filed on Dec. 21, 2001 and provisional Appl. No. 60/348,182 filed on Jan. 11, 2002.

FIELD OF THE INVENTION

The present invention relates to the novel crystal Forms III, IV, V, and the amorphous form of clopidogrel hydrogensulfate, novel processes for their preparation, compositions containing the new forms and novel processes for the preparation of Form I.

BACKGROUND OF THE INVENTION

Atherosclerosis is the buildup of plaque in the wall of the arteries leading to a thickening and a reduction in elasticity of the arteries. Atherosclerosis results from injury to the inside layer of the artery. The injury is caused by common activities and diseases such as high cholesterol, high blood pressure, smoking and infection.

Plaques form on the inner walls of the artery at these sites of injury. The plaques are mainly composed of fatty tissue and smooth muscle cells. The formation of plaque often leads to blood clotting due to platelet aggregation at the site of the injury. This clotting may result in a reduction or elimination of blood flow to vital organs, causing heart attacks or other serious conditions. The plaque may also rupture and send a blood clot through the artery, referred to as an embolus, which if deposited in a smaller blood vessel may completely block blood flow.

Antiplatelet activity is desirable in fighting the often fatal results of atherosclerosis. Clopidogrel is an inhibitor of induced platelet aggregation which acts by inhibiting the binding of adenosine diphosphate to its receptor. Clopidogrel is metabolized by the liver into active form. Its antiplatelet activity is extended in that it stops any platelet activity even up to ten days after administration.

The chemical name of clopidogrel is methyl (+)-(S)-α-(o-chlorophenyl)-6,7-dihydrothieno[3,2-c]pyridine-5(4H)-acetate. It has the following structure:

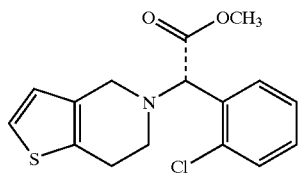

Clopidogrel's platelet inhibiting activity makes it an effective drug for reducing the incidence of ischemic strokes, heart attacks or claudication due to vascular diseases such as atherosclerosis. By inhibiting platelet aggregation, clopidogrel reduces the chance of arterial blockage, thus preventing strokes and heart attacks. U.S. Pat. No. 5,576,328 describes a method of preventing the occurrence of a secondary ischemic event by administration of clopidogrel, and is incorporated herein as a reference.

Recent studies have shown that clopidogrel is more effective in blocking platelet aggregation than aspirin and is much gentler on the gastrointestinal tract. Clopidogrel is more effective than aspirin even at much lower dosage. A dosage of 75 mg of base equivalent has been shown to be more effective than a dosage of 325 mg of aspirin. In addition to being more effective, clopidogrel produces much less gastrointestinal bleeding than aspirin.

Clopidogrel is administered as its hydrogensulfate (syn. bisulfate) salt. Clopidogrel hydrogensulfate has an empirical formula of $C_{16}H_{16}ClNO_2S.H_2SO_4$. It is currently being marketed as PLAVIX® tablets, which contain about 98 mg clopidogrel hydrogensulfate, which is the equivalent of 75 mg clopidogrel base. PLAVIX® is a white to off-white powder that is practically insoluble in water at neutral pH but highly soluble at acidic pH. It dissolves freely in methanol, somewhat in methylene chloride, and poorly in ethyl ether.

U.S. Pat. Nos. 4,847,265; 5,132,435; 6,258,961; 6,215,005 and 6,180,793, which are hereby incorporated by reference in their entirety, describe methods that can be used to prepare clopidogrel hydrogensulfate.

The present invention relates to the solid state physical properties of clopidogrel hydrogensulfate prepared by any of these or other methods. These properties can be influenced by controlling the conditions under which clopidogrel is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account when developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences because it imposes an upper limit on the rate at which an orally-administered active ingredient can reach the bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC), and can be used to distinguish some polymorphic forms from others. A particular polymorphic form may also give rise to distinct properties that may be detectable by powder X-ray diffraction, solid state $^{13}C$ NMR spectrometry and infrared spectrometry.

The discovery of new crystalline forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

U.S. Pat. No. 4,529,596 is directed to the composition of clopidogrel and methods of its use. The '596 patent teaches synthesis of clopidogrel, but fails to suggest or disclose the existence of polymorphs or the amorphous form of clopidogrel. U.S. Pat. No. 4,847,265 is directed to the enantiomer of clopidogrel, and also does not suggest or teach any polymorphs or the amorphous form of clopidogrel. These U.S. patents are incorporated herein by reference.

International Publication No. WO 99/65915 discloses two polymorphs of clopidogrel hygrogensulfate, referred to as Forms I and II, though Form I is originally disclosed in EP 281459.

According to the International Publication No. WO 99/65915, Form I has a PXRD pattern with peaks at 9.2, 10.9, 15.2, 17.9, 18.5, 20.6, 23.0, 23.2, 23.4 and 25.5±0.2 degrees two theta. Form I also has an infrared spectrum with absorption bands at 2987, 1753, 1222, 1175 and 841 cm$^{-1}$.

WO 99/65915 also discloses clopidogrel hydrogensulfate Form II, according to which has a PXRD pattern with peaks at 12.9, 13.6, 15.6, 17.7, 19.5, 21.6, 23.0, 23.3 and 24.7±0.2 degrees two theta. It has an infrared spectrum with absorption bands at 2551, 1753, 1497, 1189 and 1029 cm$^{-1}$.

According to Applicants' English translation, in Example 1B, Form I is prepared by dissolving clopidogrel camphorsulphonate in dichloromethane under a nitrogen atmosphere. A solution of potassium carbonate in water is then introduced. The organic phase is then removed, concentrated and added to acetone. The acetone solution is placed in a reactor under nitrogen and a 80% solution of sulfuric acid is added. The mixture is then distilled and cooled, followed by subsequent crystallization. The crystals are washed and dried to obtain Form I.

According to *Chemical Abstract* Accession No. 1999:811251, Form II is prepared by addition of a solution of 50 g of clopidogrel camphorsulfonate in 100 mL of dichlormethane to a solution of 9.1 g of potassium carbonate in 70 mL of water. The organic phase was separated, concentrated and dissolved in 229 mL of acetone. The acetone solution was refluxed with 7.4 g of 80% sulfuric acid under nitrogen for 2 h. The solvent was then removed to yield Form II.

Form II may also be prepared from Form I by storing aqueous mother liquor from the crystallization of Form I for 3–6 months.

Three new crystal forms of clopidogrel hydrogensulfate, designated Forms III, IV and V, plus the amorphous form of clopidogrel hydrogensulfate, and a novel process for their preparation, and preparation of Form I of clopidogrel have now been discovered.

SUMMARY OF THE INVENTION

In a first aspect, the present invention provides a new polymorph of clopidogrel hydrogensulfate, denominated Form III, and a process for its preparation. In another aspect, the present invention provides for clopidogrel hydrogensulfate characterized by a differential scanning calorimetric thermogram having an endothermic peak at about 105° C. The present invention further provides for clopidogrel hydrogensulfate characterized by a powder X-ray diffraction pattern with peaks at about 8.1, 8.7, 14.3, 15.4, 20.1, 22.3, 22.5, 23.5, and 24.1±0.2 degrees two theta. The present invention also provides for clopidogrel hydrogensulfate characterized by a FTIR spectrum with peaks at about 581, 707, 755, 971, 1057, 1196, 1252, 1436, 1476, 1748, 2590, 2670 and 2963 cm$^{-1}$.

In another aspect, the present invention provides for a process for preparing clopidogrel hydrogensulfate Form III comprises the steps of preparing a solution of clopidogrel hydrogensulfate in 1-butanol, removing the 1-butanol from the solution to obtain a residue, adding an antisolvent to the residue to cause formation of a precipitate, separating the precipitate and drying the precipitate.

The present invention also provides for the new composition of the amorphous form of clopidogrel hydrogensulfate. The present invention further provides clopidogrel hydrogensulfate characterized by a FTIR spectrum with peaks at about 583, 723, 762, 846, 1040, 1167, 1223, 1438, 1478, 1638, 1752, 2585 and 2960 cm$^{-1}$. In another aspect, the present invention provides for clopidogrel hydrogensulfate having a PXRD pattern as substantially depicted in FIG. 4.

In another aspect, the present invention provides a process for preparing the amorphous form of clopidogrel hydrogensulfate comprising the steps of preparing a solution of clopidogrel hydrogensulfate in an alcohol selected from the group consisting of methanol and ethanol, adding the solution to an antisolvent to cause formation of a precipitate and separating the precipitate.

In another aspect, the present invention provides a process for preparing the amorphous form of clopidogrel hydrogensulfate comprising the steps of preparing a solution of clopidogrel hydrogensulfate in an alcohol selected from the group consisting of methanol and ethanol, removing the alcohol from the solution to obtain a residue, adding an antisolvent to the residue to cause formation of a precipitate and separating the precipitate.

In another aspect, the present invention provides a process for preparing the amorphous form of clopidogrel hydrogensulfate comprising the steps of preparing a solution of clopidogrel hydrogensulfate in an alcohol selected from the group consisting of methanol and ethanol, adding the solution to an antisolvent and removing the alcohol and the antisolvent.

In another aspect, the present invention provides a process for preparing the amorphous form of clopidogrel hydrogensulfate comprising preparing a solution of clopidogrel hydrogensulfate in acetone and removing the acetone.

In another aspect, the present invention provides a process for preparing clopidogrel hydrogensulfate Form I comprising the steps of contacting amorphous clopidogrel hydrogensulfate with an ether and separating the clopidogrel hydrogensulfate Form I.

In another aspect, the present invention relates to clopidogrel hydrogensulfate Form IV. The present invention further provides clopidogrel hydrogensulfate characterized by a PXRD pattern with peaks at about 22.0, 25.9, 26.9, 27.4, 28.1, 28.6 and 28.9±0.2 degrees two theta. In another aspect, the present invention provides clopidogrel hydrogensulfate characterized by a DTG thermogram with an endothermic peak at about 160–170° C. The present invention further provides for clopidogrel hydrogensulfate characterized by a FTIR spectrum with peaks at about 618, 769, 842, 893, 935, 974, 1038, 1116, 1370, 1384 cm$^{-1}$.

In another aspect, the present invention provides a process for preparing clopidogrel hydrogensulfate Form IV comprising forming a precipitate from a solution of clopidogrel hydrogensulfate and isopropanol and separating the precipitate.

In another aspect, the present invention relates to clopidogrel hydrogensulfate Form V. The present invention also provides for clopidogrel hydrogensulfate characterized by a PXRD diffraction pattern with peaks at about 25.5, 26.6, 27.8 and 28.5±0.2 degrees two theta. The present invention further provides for clopidogrel hydrogensulfate characterized by a DSC profile with an endothermic peak at about 126–132° C. The present invention also provides for clopidogrel hydrogensulfate characterized by a FTIR spectrum with peaks at about 623, 743, 802, 817, 843, 963, 972, 1028 and 1374 cm$^{-1}$.

The present invention provides a process for preparing clopidogrel hydrogensulfate Form V comprising the steps of dissolving clopidogrel hydrogensulfate in 2-butanol to form a solution, adding an antisolvent to the solution to cause formation of a precipitate and separating the precipitate.

In another aspect, the present invention provides a process for preparing clopidogrel hydrogensulfate Form V comprising the steps of dissolving clopidogrel hydrogensulfate in 2-butanol to form a solution, removing the 2-butanol from the solution to obtain a residue, adding an antisolvent to the residue to cause formation of a precipitate and separating the precipitate.

The present invention also provides for pharmaceutical compositions of clopidogrel and methods of their use in order to inhibit platelet aggregation.

DETAILED DESCRIPTION OF THE INVENTION

As used herein, the terms "IPA", "iospropanol", "isopropyl alcohol" and "2-propanol" refer to the same alcohol.

The present invention provides new polymorphs of clopidogrel hydrogensulfate and novel amorphous form. The various forms are obtained by using different alcohols.

Figure 1:
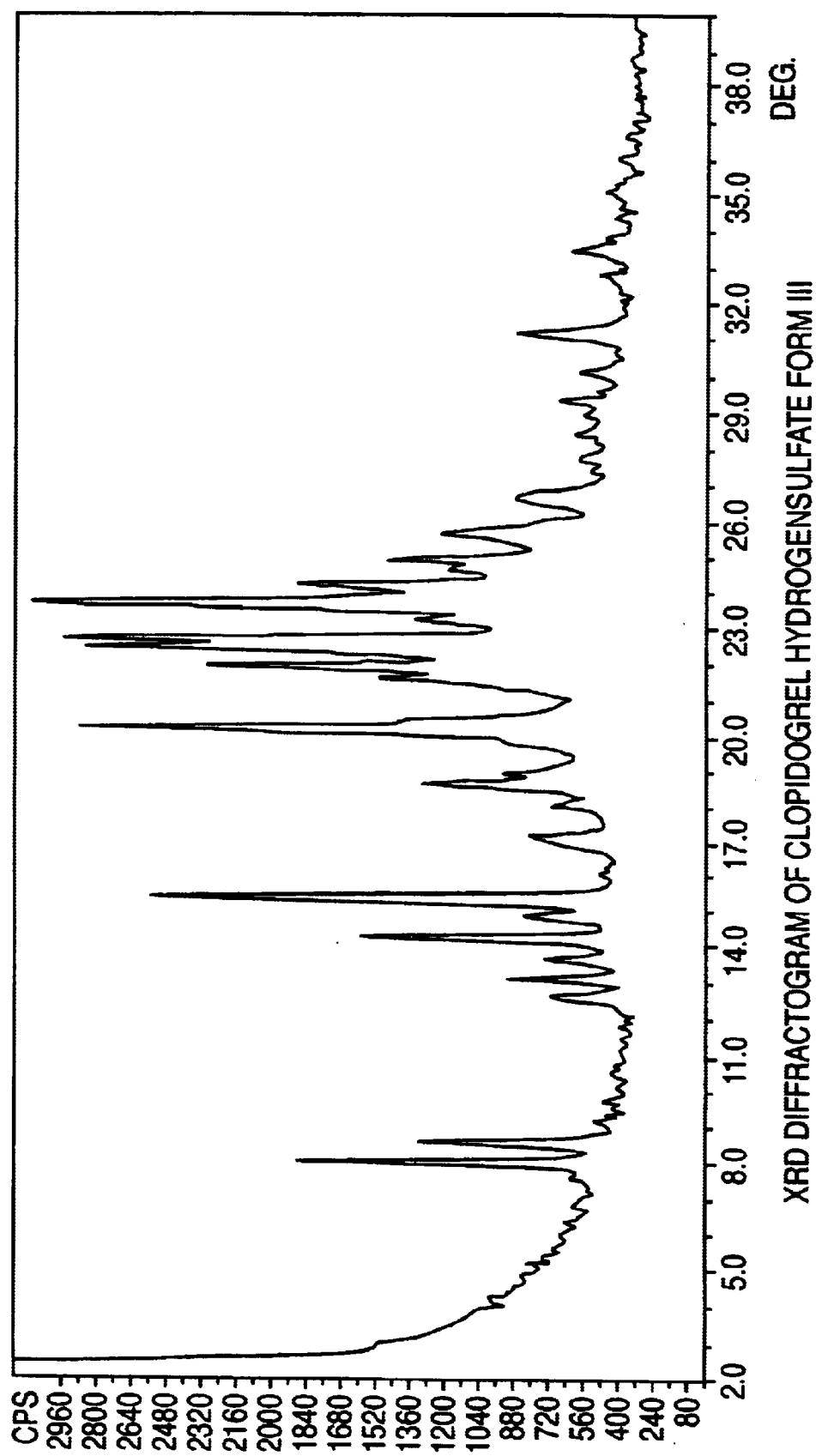
FIG. 1 is a powder X-ray diffraction pattern of clopidogrel hydrogensulfate Form III.

In a first aspect, the present invention provides a new crystalline form of clopidogrel hydrogensulfate, designated Form III. Clopidogrel hydrogensulfate Form III is characterized by a powder X-ray diffraction pattern (FIG. 1) with peaks at about 8.1, 8.7, 14.3, 15.4, 20.1, 22.3, 22.5, 23.5, and 24.1±0.2 degrees two-theta. Powder X-ray diffraction patterns were obtained by methods known in the art using a Scintag X-ray powder diffractometer, a variable goniometer, an X-Ray tube with Cu target anode and a solid state detector. A round standard aluminum sample holder with a round zero background quartz plate was used. Scans were performed over a range of 2 to 40 degrees two-theta, continuously, with a scan rate of 3 degrees/min.

Figure 2:
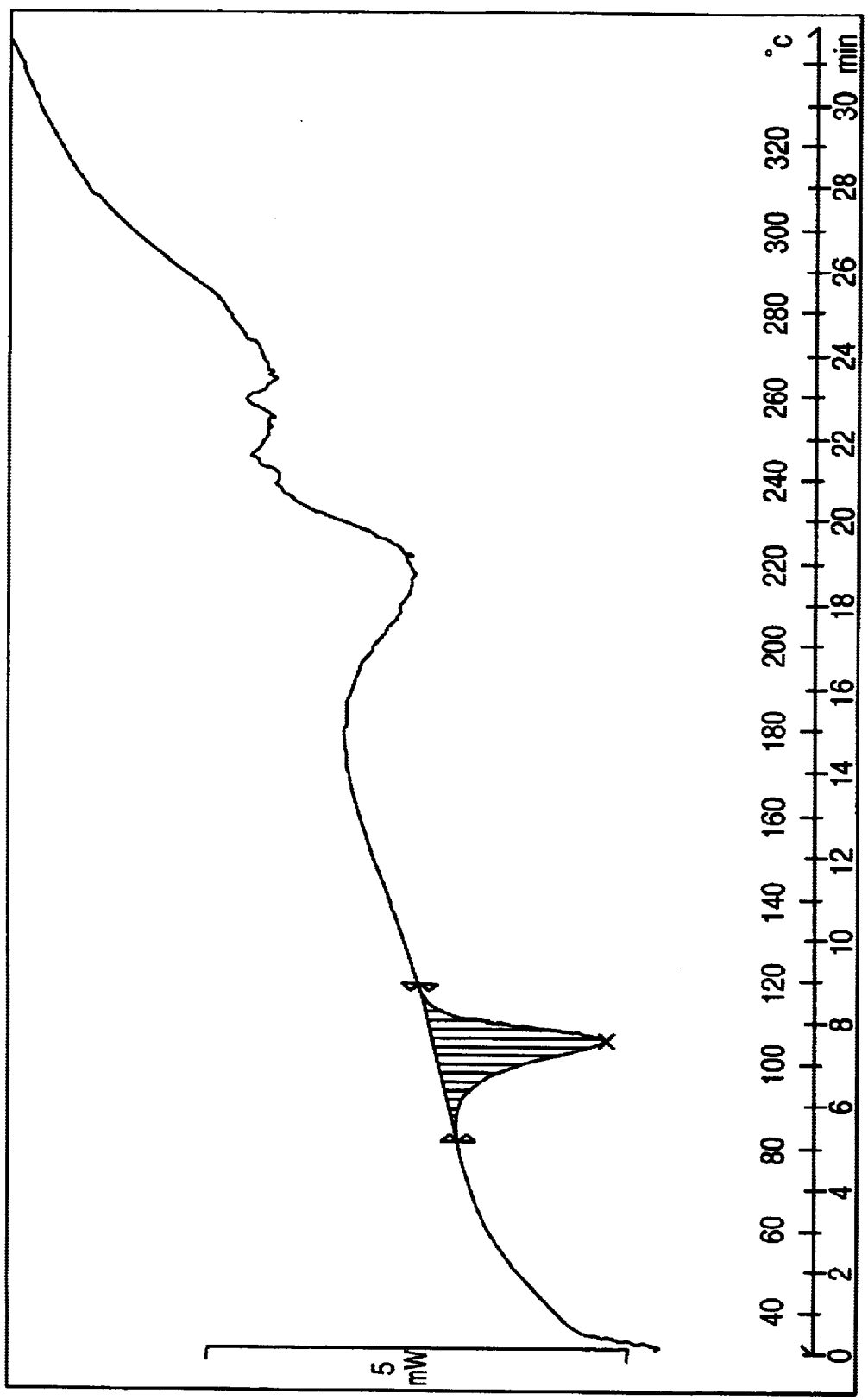
FIG. 2 is a differential scanning calorimetric (DSC) thermogram of clopidogrel hydrogensulfate Form III.

Clopidogrel hydrogensulfate Form III produces a differential scanning calorimetric (DSC) thermogram (FIG. 2) having a maximum endotherm of about 105° C. The DSC thermogram was obtained using a DSC Mettler 821 Stare. The temperature range of scans was 30–350° C. at a rate of 10° C./min. The weight of the sample was 2–5 mg. The sample was purged with nitrogen gas at a flow rate of 40 mL/min. Standard 40 µl aluminum crucibles having lids with three small holes were used.

Figure 3:
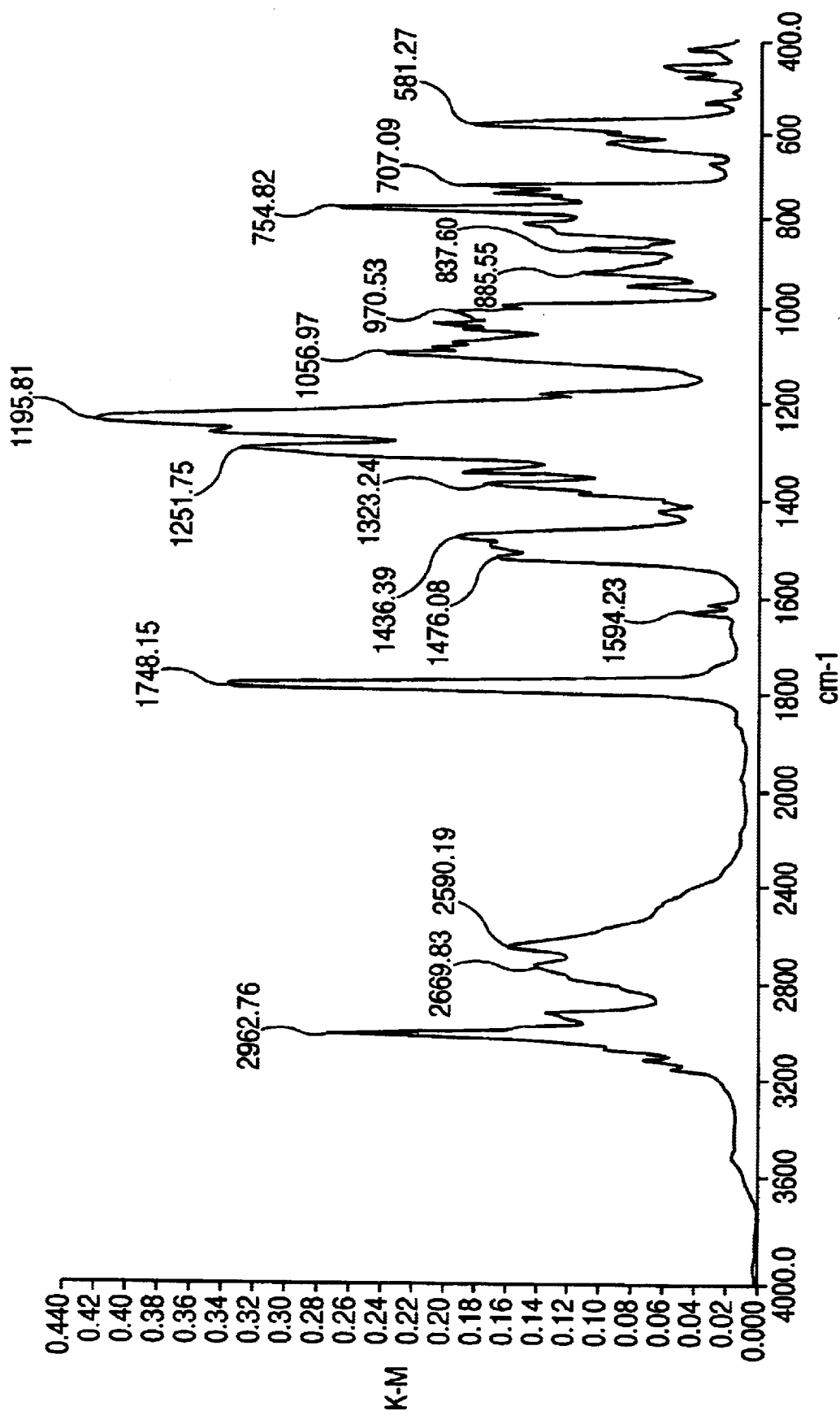
FIG. 3 is a FTIR spectrum of clopidogrel hydrogensulfate Form III.

Clopidogrel hydrogensulfate Form III produces a FTIR spectrum (FIG. 3) with characteristic absorption bands at about 581, 707, 755, 971, 1057, 1196, 1252, 1436, 1476, 1748, 2590, 2670 and 2963 cm$^{-1}$. The FTIR spectrum of clopidogrel hydrogensulfate Form III has additional absorption bands at about 838, 886 and 1594 cm$^{-1}$. To obtain the FTIR results, we utilized a Perkin-Elmer Spectrum One FTIR spectrometer, using the diffuse reflectance technique. The spectrum was recorded from 4000–400 cm$^{-1}$. Sixteen scans were taken at a resolution of 4.0 cm$^{-1}$.

The present invention further provides a process for preparing clopidogrel hydrogensulfate Form III comprising the steps of preparing a solution of clopidogrel hydrogensulfate and 1-butanol, removing the 1-butanol to obtain a residue, adding an antisolvent to the residue to cause formation of a precipitate, separating the precipitate and drying the precipitate.

In the process, clopidogrel hydrogensulfate is mixed with a sufficient amount of alcohol to dissolve the clopidogrel hydrogensulfate at or below the reflux temperature of the alcohol. To fully dissolve the clopidogrel hydrogensulfate, the mixture may be heated to a temperature up to reflux of the alcohol. Preferably, the mixture refluxed for about 30 minutes. When preparing the solution with clopidogrel base and sulfuric acid, the solution is preferably refluxed for longer periods of time, such as about 2 hours. One skilled in the art may appreciate that minor differences in the temperature and times may produce the same result, and other temperatures and times may produce the same result under other conditions.

In the most preferred embodiment, the alcohol is evaporated under ambient or reduced pressure after cooling, with intermediate cooling optional. Preferably, the solution is cooled to room temperature and the alcohol is evaporated under reduced pressure. A residue remains after evaporation.

An antisolvent is then added to the residue. Preferably, the antisolvent is ether. More preferably, each one of the ether's alkyl radical groups connected to the oxygen atom is independently selected from the group consisting of methyl, ethyl, propyl, isopropyl, butyl, 1-butyl, 2-butyl and t-butyl. Most preferably, the ether is diethyl ether or methyl t-butyl ether.

The mixture of residue and antisolvent may then be stirred for one or two days, preferably for longer times when staring with clopidogrel base. A precipitate begins to form. The precipitate is then separated from the mixture. One skilled in the art may appreciate that there are many ways to separate the precipitate from the mixture. Preferably, the precipitate is separated by filtration. After separation, the precipitate may optionally be washed with an organic solvent such as diethyl ether to remove impurities.

The separated precipitate is then dried under either ambient or reduced pressure. In a preferred embodiment, the precipitate is dried under a vacuum. Preferably, the precipitate is heated to accelerate the drying process. More preferably, it is heated from about 40° C. to about 80° C. Most preferably, it is heated to about 50° C.–65° C. for about 24 hours in a vacuum oven. One skilled in the art may appreciate that many ways exist for drying a compound, and that by manipulating the conditions, other temperatures, pressures and time periods would suffice.

Clopidogrel Form III may be obtained in yields of about 97%, which shows the high efficiency and effectiveness of this novel process.

In another aspect, this invention provides novel amorphous clopidogrel hydrogensulfate. In accordance with the invention, amorphous clopidogrel hydrogensulfate is highly pure. More preferably, it is essentially free of crystalline clopidogrel hydrogensulfate. Most preferably, the amorphous clopidogrel hydrogensulfate is free of crystalline clopidogrel hydrogensulfate within the detection limits of a powder X-ray diffractometer comparable to the instrumentation described above. The purity of clopidogrel hydrogensulfate can be assessed by a comparison of the PXRD pattern of an unknown sample with those of mixtures of authentic pure amorphous and authentic pure crystalline clopidogrel hydrogensulfate.

Figure 4:
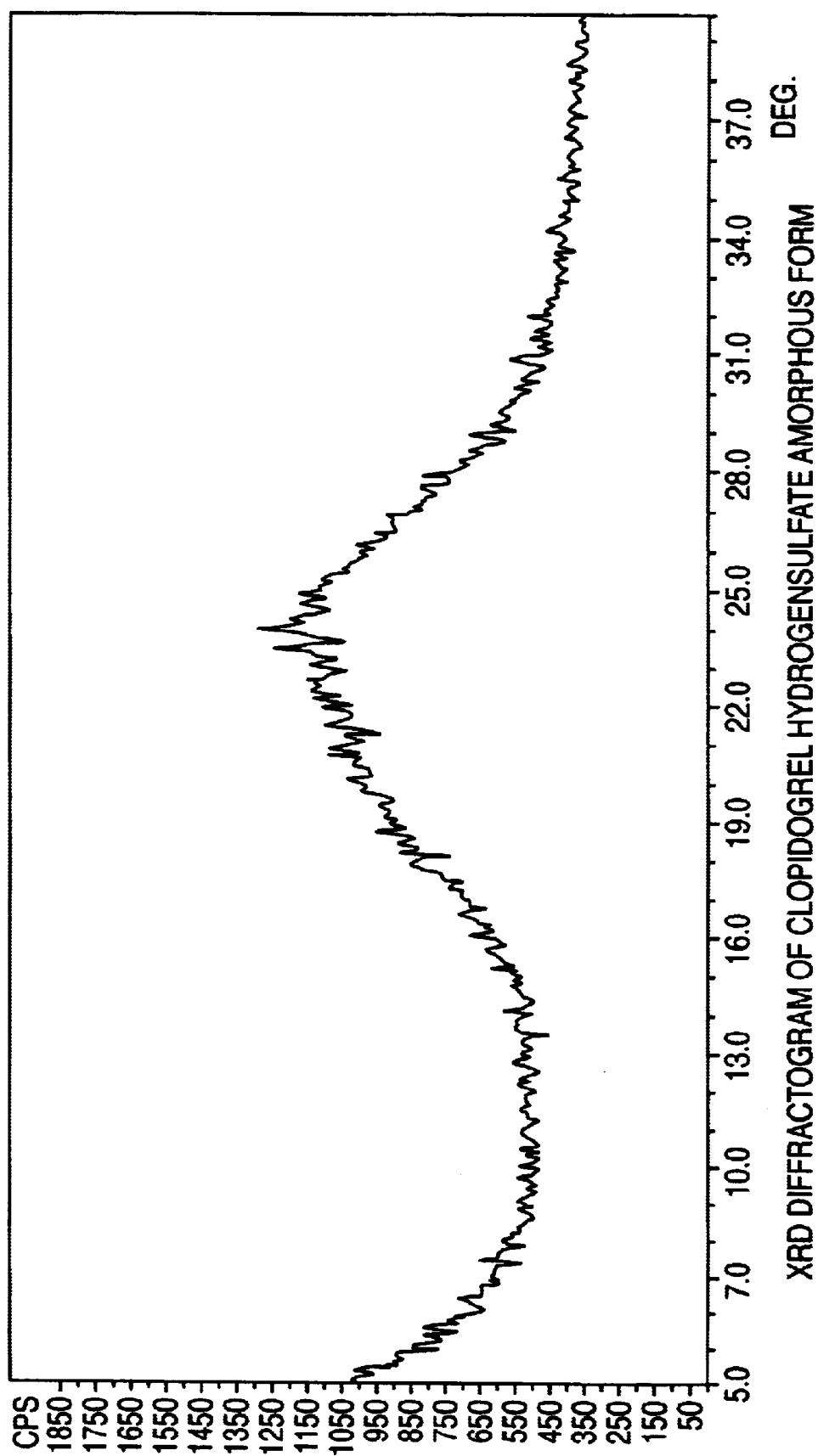
FIG. 4 is a powder X-ray diffraction (PXRD) pattern of clopidogrel hydrogensulfate amorphous form.

The amorphous character and purity of the material we have produced is confirmed by a powder X-ray diffraction pattern obtained from a sample thereof, which is provided as FIG. 4. The pattern is without intense focused reflections and is featureless except for a halo with a maximum centered at about 24 degrees two-theta.

Figure 5:
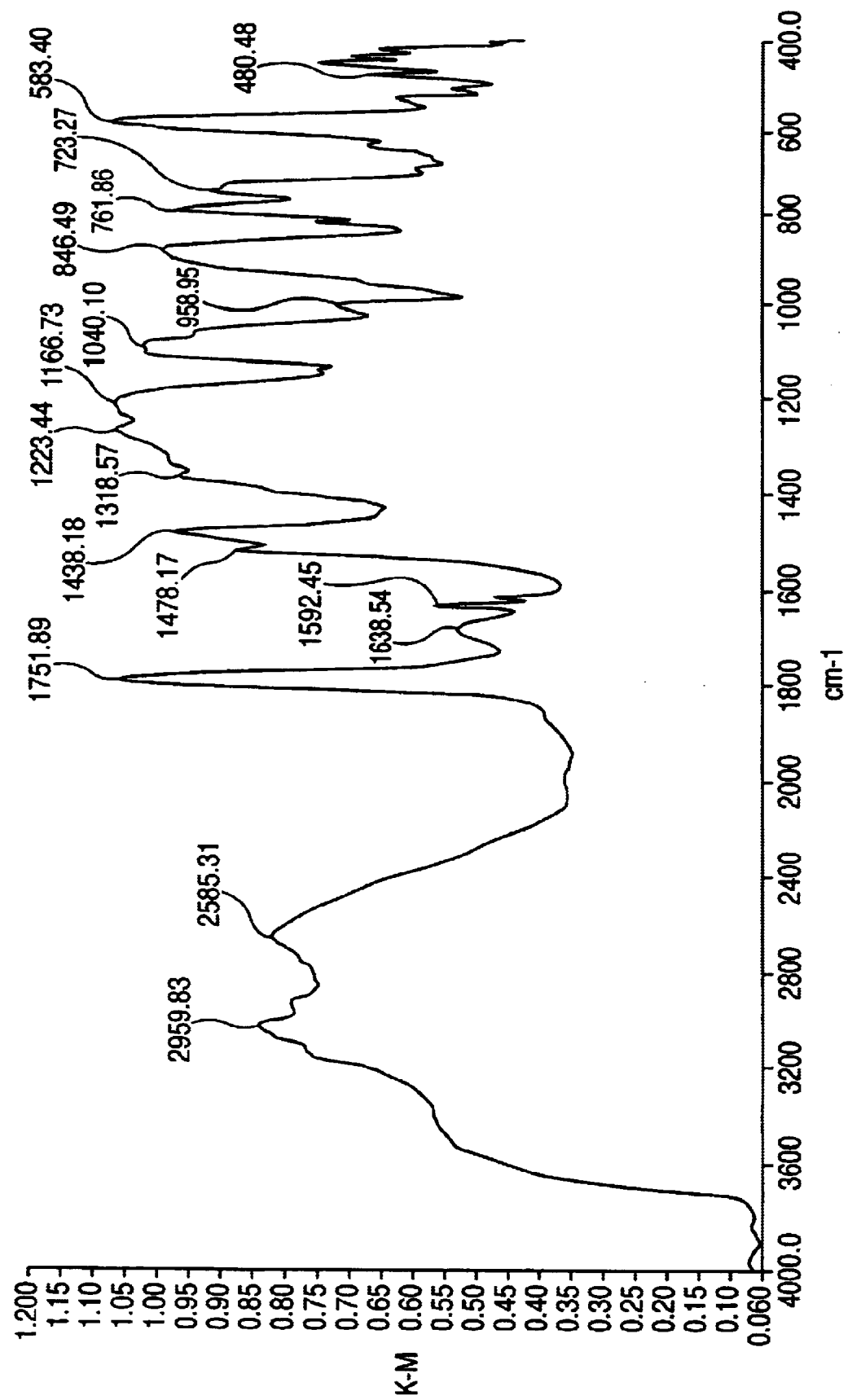
FIG. 5 is a FTIR spectrum of clopidogrel hydrogensulfate amorphous form.

The amorphous form has a FTIR spectrum (FIG. 5) with peaks at about 583, 723, 762, 846, 1040, 1167, 1223, 1438, 1478, 1638, 1752, 2585 and 2960 $cm^{-1}$.

The invention further provides a process for preparing amorphous form of clopidogrel hydrogensulfate comprising the steps of preparing a solution of clopidogrel hydrogensulfate in methanol or ethanol, and adding the solution to an antisolvent to cause formation of a precipitate and separating the precipitate.

The alcoholic solution of clopidogrel hydrogensulfate may be heated to increase the solubility of clopidogrel hydrogensulfate in the alcohol. Preferably, the solution is heated from about room temperature to about reflux, with temperatures at or near reflux being most preferred. After dissolution, the solution may be cooled, preferably to room temperature.

The alcohol may optionally be removed from the solution to obtain a foam or an oily residue. Preferably, the alcohol is removed by evaporation. The alcohol may be evaporated under ambient or reduced pressure and optionally heated to accelerate the evaporation. The antisolvent in such a case is then added to the foam or the oily residue.

Alternatively, the solution of clopidogrel hydrogensulfate and alcohol may be added to the antisolvent to cause the formation of a precipitate. Preferably, the solution is added slowly to the antisolvent. Preferably, the antisolvent is an ether. Each alkyl radical of the ether may be independently selected from the group consisting of methyl, ethyl, propyl, isopropyl, butyl, 1-butyl, 2-butyl and tert-butyl. In one preferred embodiment, the ether is methyl t-butyl ether. In another preferred embodiment, the ether is diethyl ether.

A precipitate forms in the ether. The precipitate should be separated from the ether at an early stage, preferably within a few hours. Otherwise, the amorphous form will change to Form I, resulting in a lower yield.

The precipitate may be separated by techniques well-known in the art. Preferably, the precipitate is separated by filtration. Optionally, vacuum filtration may be utilized.

The precipitate may be dried under ambient or reduced pressure. Preferably, the precipitate is heated in a vacuum oven for about 24 hours. More preferably, the precipitate is heated to a temperature of about 40° C. to about 70° C. Most preferably, it is heated to about 50° C. for about 24 hours.

The present invention also provides a process for preparing amorphous clopidogrel hydrogensulfate comprising the steps of preparing a solution of clopidogrel hydrogensulfate and methanol or ethanol, adding the solution to an antisolvent, and removing the alcohol and the antisolvent.

In one preferred embodiment, the antisolvent is a one ring aromatic compound, such as toluene, benzene or xylene. Most preferably, the one ring aromatic compound is toluene.

Clopidogrel hydrogensulfate is first dissolved in the alcohol to form a solution. After dissolving the clopidogrel hydrogensulfate in the alcohol, the solution is added to the antisolvent. In a less preferred embodiment, the solution is concentrated before addition to the antisolvent. Preferably, the antisolvent is heated to a temperature of about room temperature to reflux so that the clopidogrel hydrogensulfate becomes more soluble in the antisolvent, with temperatures at or near reflux being preferred. Most preferably, the antisolvent is heated to reflux temperature. Besides heating the antisolvent, the mixture may be added to the antisolvent at a substantially slow rate to increase the total amount of clopidogrel taken up by the antisolvent.

After addition of the mixture to the antisolvent, the resulting mixture is preferably cooled to about room temperature, though one skilled in the art may appreciate that other temperatures may achieve the same result. To obtain the amorphous form, the antisolvent and the alcohol are removed, preferably by evaporation, to leave the amorphous form.

Evaporation may occur under ambient or reduced pressure, and the solution may be heated to accelerate the evaporation process.

The present invention provides a process for preparing the amorphous form of clopidogrel hydrogensulfate comprising the steps of preparing a solution of clopidogrel hydrogensulfate in acetone and removing acetone to obtain the amorphous form. The mixture of clopidogrel hydrogensulfate and acetone is heated to form a solution. Preferably, the mixture is heated to a temperature where a homogeneous solution forms. Most preferably, the mixture is heated to about reflux for a few hours.

After heating, the solution is preferably cooled to about room temperature. The solution may be stirred. Preferably, the solution is stirred for a few hours. After stirring, the acetone is removed to obtain a powder, which is the amorphous form of clopidogrel hydrogensulfate. Preferably, the acetone is removed by evaporation. To accelerate the drying process, the pressure may be reduced and the temperature may be raised. One skilled in the art would appreciate that preparation of the amorphous form may be possible under other conditions.

The present invention also provides a process for preparing clopidogrel hydrogensulfate Form I and mixtures of clopidogrel Form I and amorphous clopidogrel hydrogensulfate. The amorphous form converts into Form I over time when suspended in an ether. Preferably, the ether is methyl t-butyl ether or diethyl ether. One skilled in the art may appreciate that the ratio of Form I to the amorphous form increases with time, and that, through routine experimentation, the ratio of the forms to each other may be determined for any specific time.

The examples illustrate that the amorphous form of clopidogrel hydrogensulfate undergoes a transformation to Form I in an ether, particularly in the time period from about 45 minutes to one hour. To obtain substantially Form I, clopidogrel hydrogensulfate is suspended in the ether for preferably one hour, with longer periods of time, such as four and eight hours, being most preferred. The transformation time may be longer if the starting material is clopidogrel free base rather than clopidogrel hydrogensulfate.

As the examples illustrate and one skilled in the art may appreciate, it is possible to obtain clopidogrel hydrogensulfate Form I from clopidogrel hydrogensulfate through the use of the amorphous form as an intermediate. First the amorphous form is obtained as illustrated, and then suspended in an ether to obtain Form I. The examples of the present invention obtain Form I through this mechanism.

Figure 6:
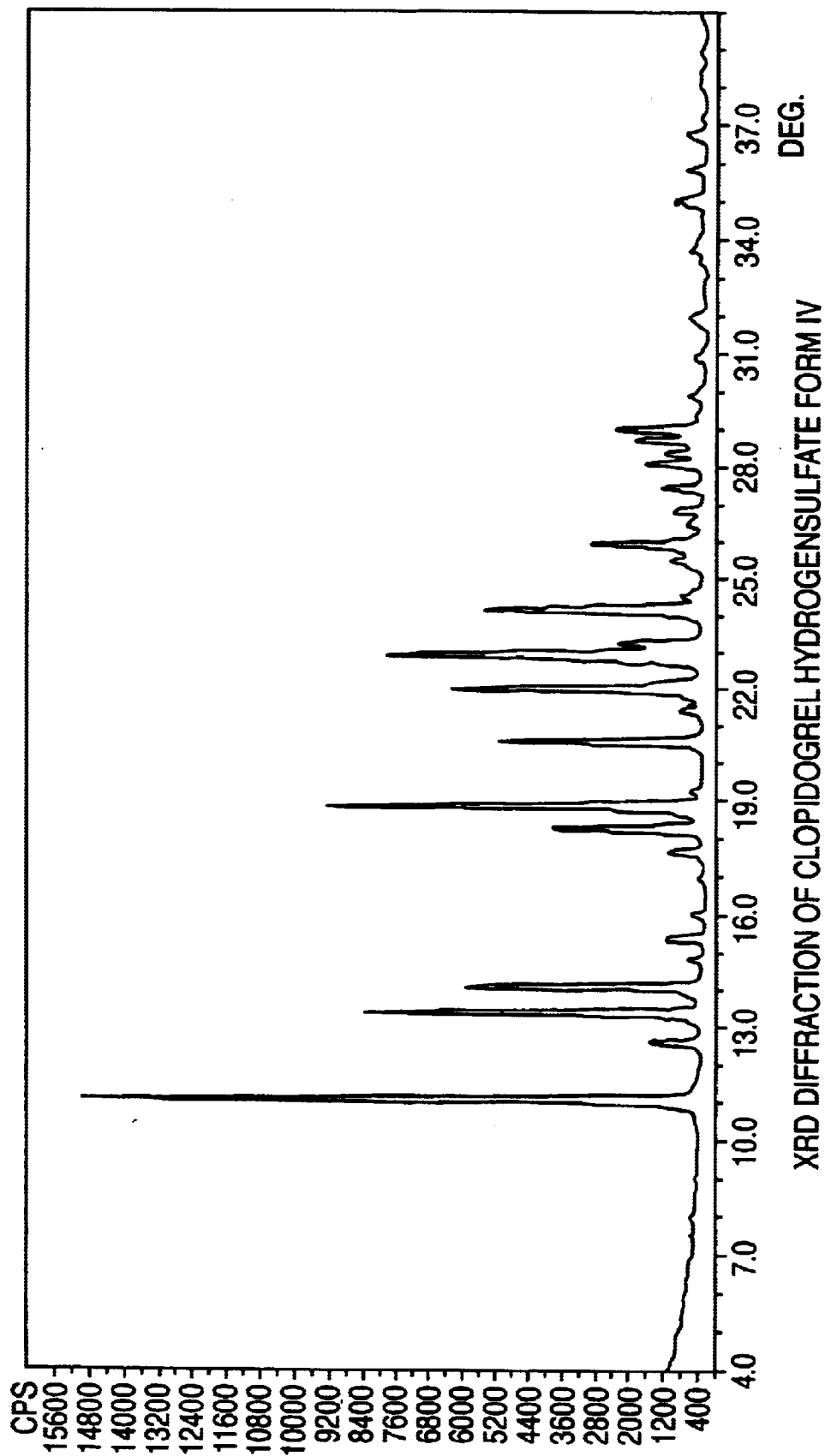
FIG. 6 is a PXRD pattern of clopidogrel hydrogensulfate Form IV.

The present invention also provides clopidogrel hydrogensulfate Form IV. Clopidogrel hydrogensulfate Form IV is characterized by powder X-Ray diffraction (PXRD), thermal analysis and FTIR spectroscopy. The clopidogrel hydrogensulfate Form IV of the present invention is characterized by a PXRD pattern (FIG. 6) with peaks at about 22.0, 25.9, 26.9, 27.4, 28.1, 28.6 and 28.9±0.2 degrees two theta. More particularly, clopidogrel hydrogensulfate Form IV is characterized by a PXRD pattern with peaks at about 11.0, 12.5, 13.3, 14.0, 17.6, 18.2, 18.8, 20.5, 22.0, 22.9, 24.1, 25.9, 26.9, 27.4, 28.1, 28.6 and 28.9±0.2 degrees two theta.

Figure 7:
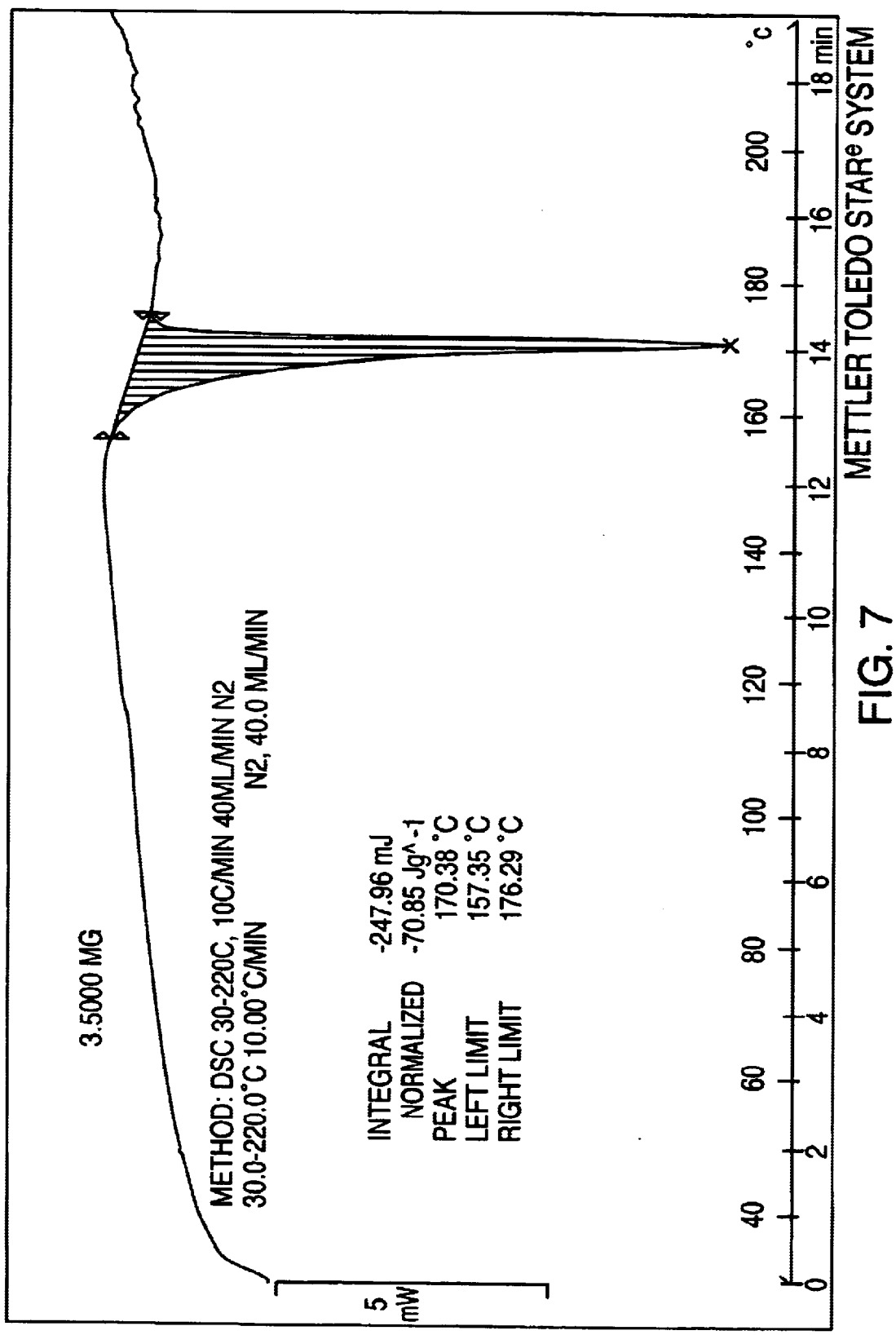
FIG. 7 is a DTG thermogram of clopidogrel hydrogensulfate Form IV.
Figure 8:
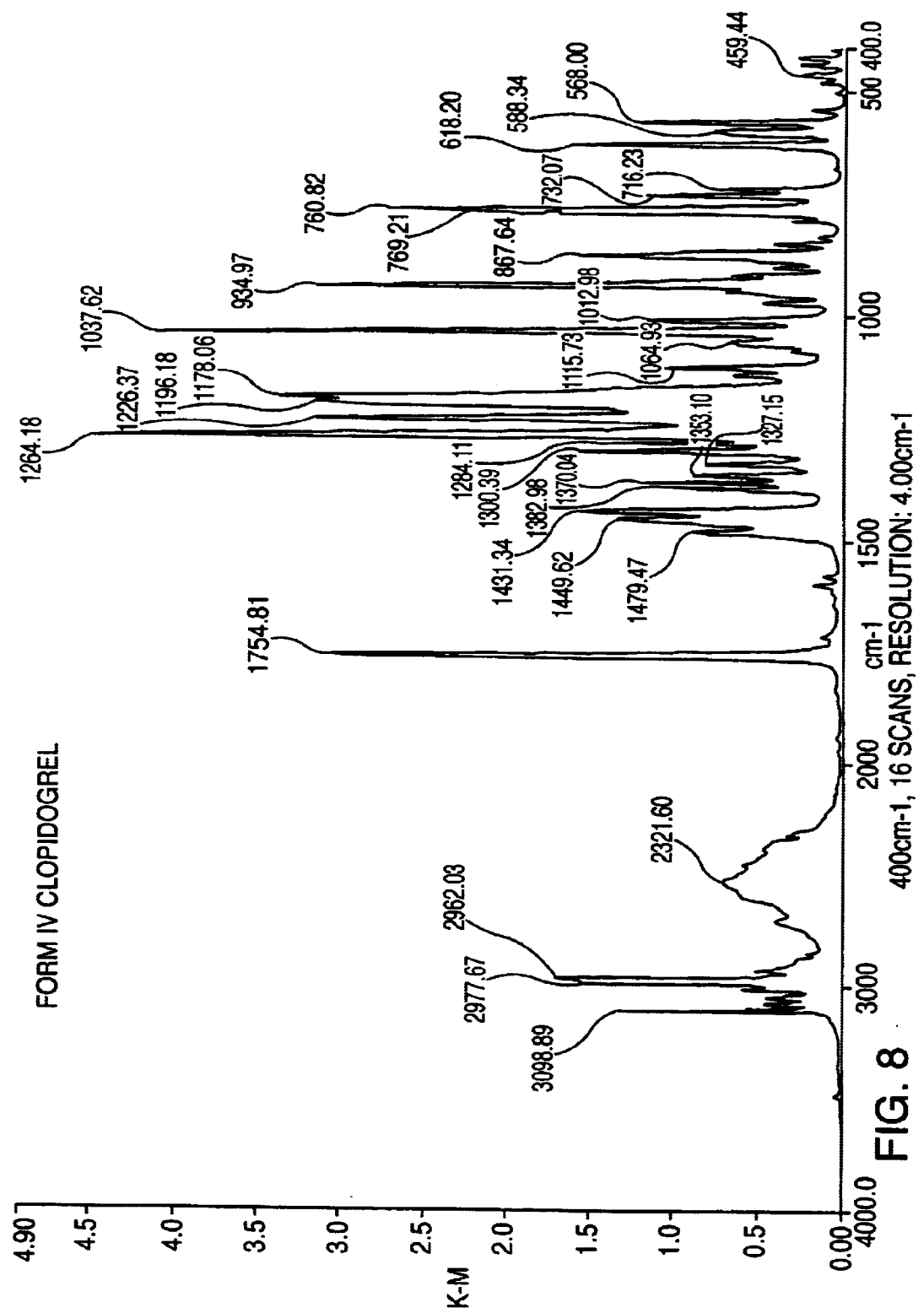
FIG. 8 is a FTIR spectrum of clopidogrel hydrogensulfate Form IV.

Clopidogrel hydrogensulfate Form IV is also characterized by Differential Thermal Gravimetry (DTG) (10° C./min, nitrogen atmosphere). The DTG profile of clopidogrel hydrogensulfate Form IV (FIG. 7) is characterized by an endothermic peak at about 160–170° C. A sharp weight loss is observed at about 145° C. due to decomposition. Clopidogrel hydrogensulfate Form IV is also characterized by a FTIR spectrum (FIG. 8) with peaks at about 618, 769, 842, 893, 935, 974, 1038, 1116, 1370, 1384 $cm^{-1}$.

The present invention provides a process for preparing clopidogrel hydrogensulfate Form IV comprising the steps of forming a precipitate from a solution of clopidogrel hydrogensulfate in isopropanol and separating the precipitate.

Clopidogrel hydrogensulfate is dissolved in isopropanol to form a solution. Preferably, the isopropanol is heated to about reflux, before the addition of the clopidogrel hydrogensulfate, to make the isopropanol substantially soluble for the clopidogrel hydrogensulfate. The resulting solution is then cooled to about room temperature. One skilled in the art appreciates that other conditions and temperatures may have the same result.

In one embodiment, the cooled solution is allowed to sit at room temperature until precipitation occurs. The solution may optionally be stirred. After stirring for a few hours, precipitation occurs. The precipitate is suspended in the isopropanol and is subsequently separated. The precipitate may be separated according to methods well known in the prior art, such as by filtering, decanting and centrifugation, filtering being the most preferred method.

After separating the precipitate, it may optionally be dried. To dry, the precipitate may be heated, or the pressure reduced to accelerate the drying process. Preferably, a vacuum oven is used to heat the precipitate for about 16 hours at a temperature of about 50° C. The result of this process is clopidogrel hydrogensulfate Form IV.

In another embodiment, after cooling the solution, the solvent is removed to leave a dry residue. The solvent is preferably removed by evaporation. The pressure may be reduced to accelerate the drying process. Analysis of the residue confirmed that it is clopidogrel hydrogensulfate Form IV. With this embodiment, a subsequent separation and drying step is not necessary since the obtained residue is already dry and separated from the solvent. In other words, evaporation causes precipitation and separation, and further dries the product.

The process for preparation of Form IV does not require an additional step of using an antisolvent.

The present invention also provides for clopidogrel hydrogensulfate Form V. Clopidogrel hydrogensulfate Form V is characterized by PXRD, thermal analysis and by FTIR spectroscopy.

Figure 9:
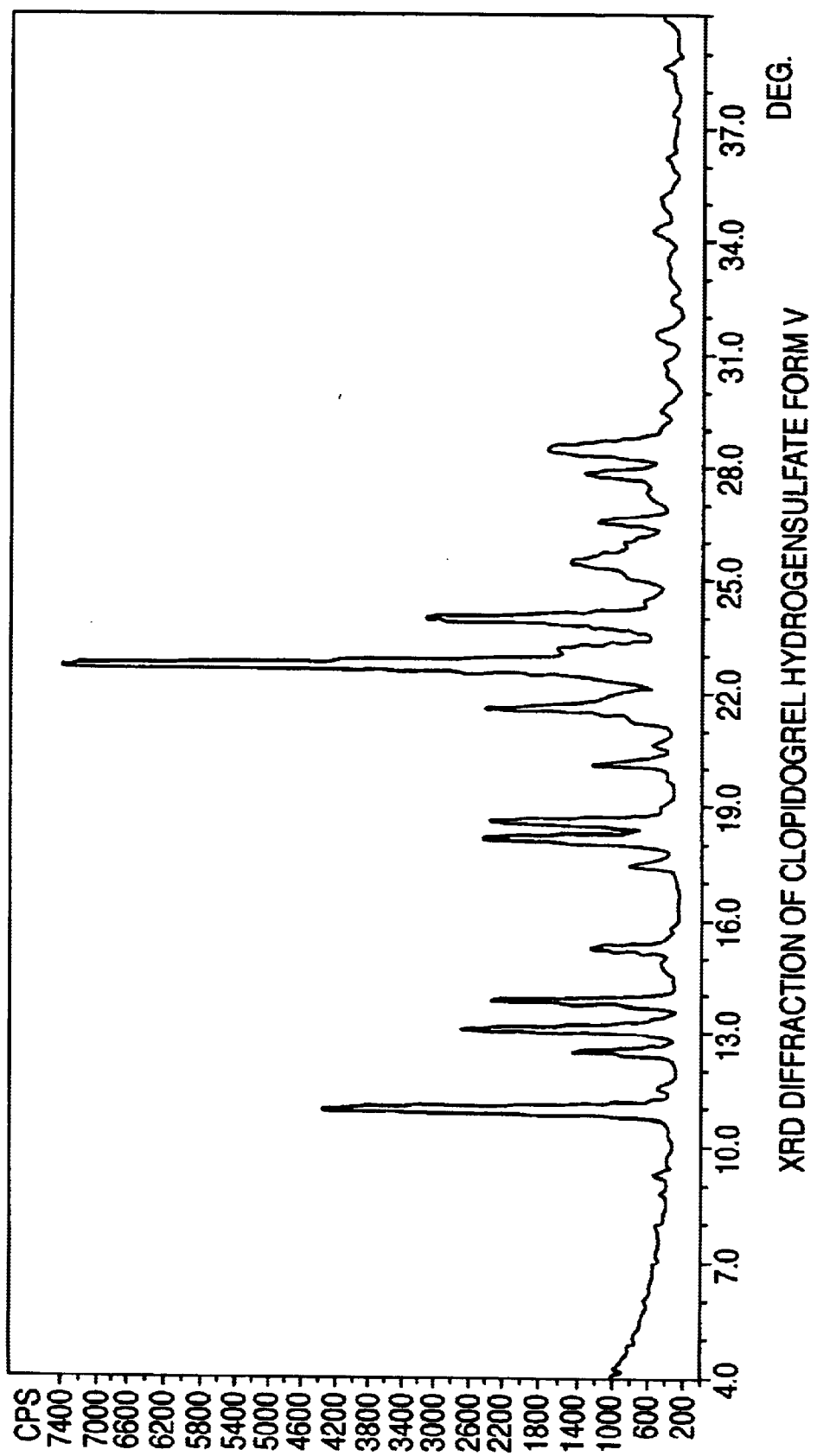
FIG. 9 is a PXRD pattern of clopidogrel hydrogensulfate Form V.

Clopidogrel hydrogensulfate Form V is characterized a PXRD diffraction pattern (FIG. 9) with peaks at about 25.5, 26.6, 27.8 and 28.5±0.2 degrees two theta. Clopidogrel hydrogensulfate Form V is particularly characterized by a PXRD diffraction pattern with peaks at about 11.0, 12.4, 13.1, 13.8, 15.2, 17.5, 18.1, 18.6, 20.2, 21.6, 22.7, 24.0, 25.5, 26.6, 27.8 and 28.5±0.2 degrees two theta.

Figure 10:
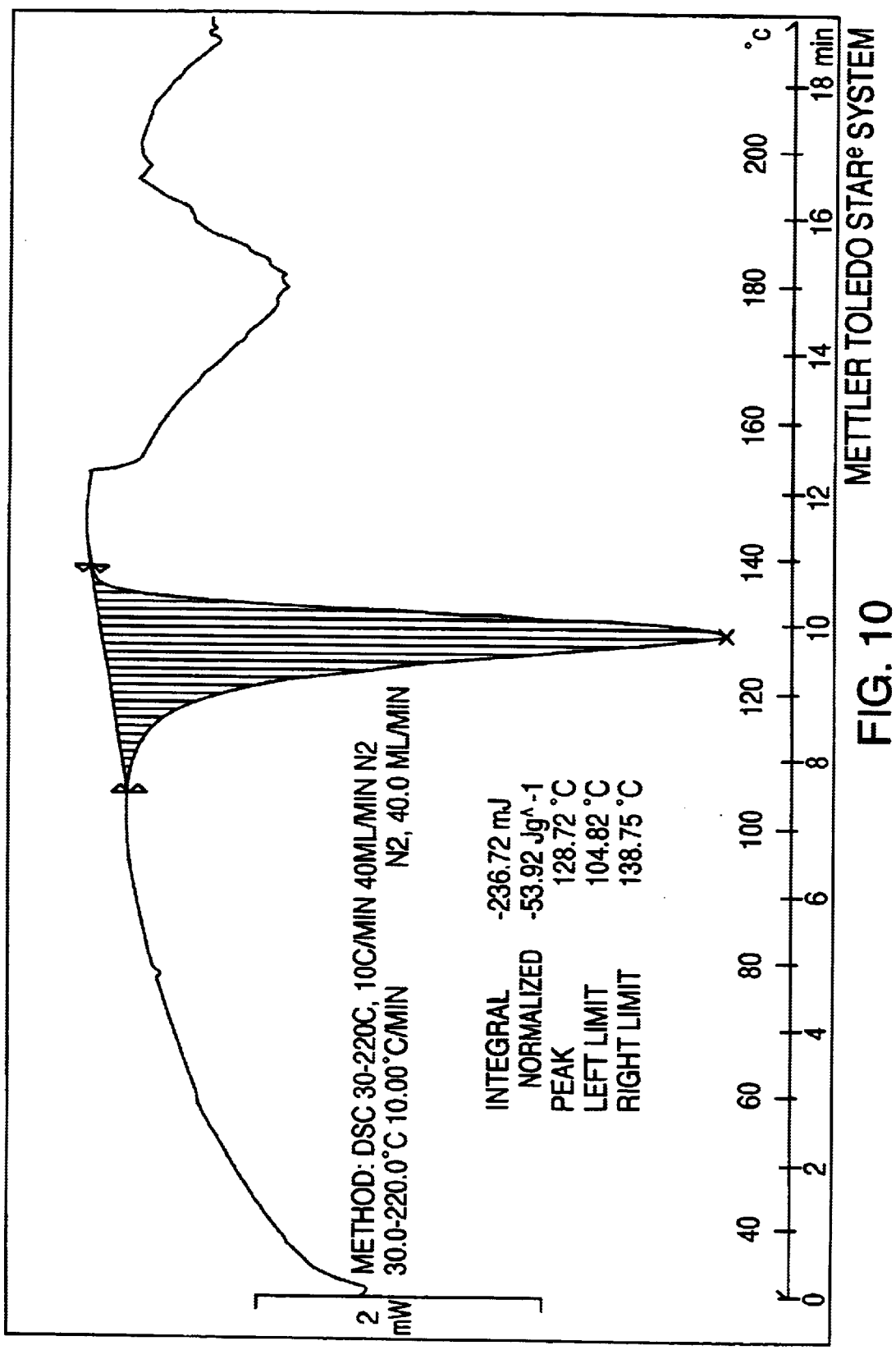
FIG. 10 is a DSC thermogram of clopidogrel hydrogensulfate Form V.
Figure 11:
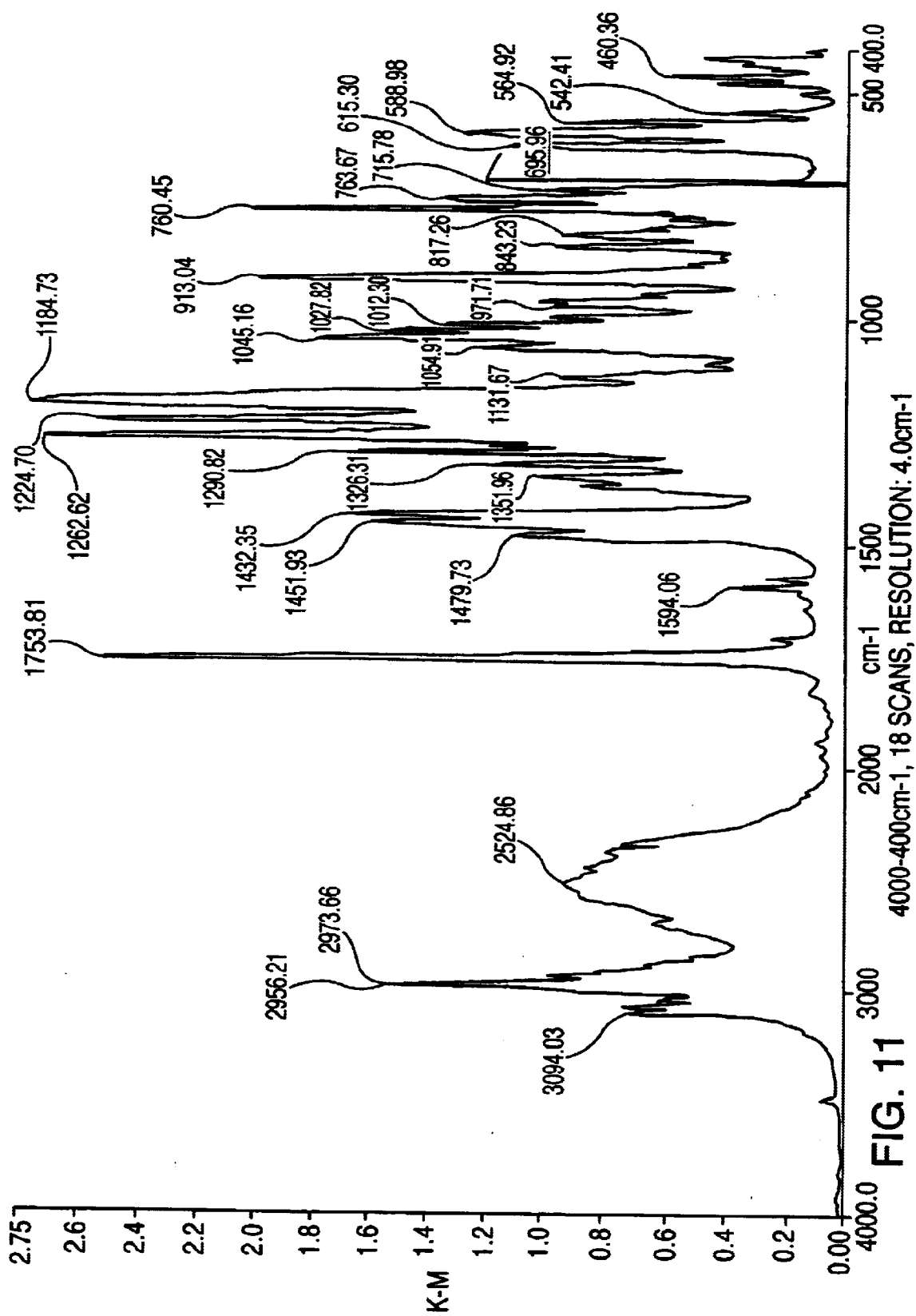
FIG. 11 is a FTIR spectrum of clopidogrel hydrogensulfate Form V.

Clopidogrel hydrogensulfate Form V is characterized by Differential Scanning Calorimetry (DSC) (10° C./min, Nitrogen atmosphere). DSC profile of clopidogrel hydrogensulfate Form V (FIG. 10) is characterized by a sharp endothermic peak at about 126–132° C. Clopidogrel hydrogensulfate Form V is also characterized by a FTIR spectrum (FIG. 11) with peaks at about 623, 743, 802, 817, 843, 963, 972, 1028 and 1374 $cm^{-1}$.

The present invention provides a process for preparing clopidogrel Form V comprising the steps of dissolving clopidogrel hydrogensulfate in 2-butanol to form a solution, adding an antisolvent to the solution to cause formation of a precipitate and separating the precipitate. The precipitate may optionally be dried. Preferably, the precipitate is dried under reduced pressure and at elevated temperature. Most preferably, the precipitate is dried in a vacuum oven for about 24 hours at a temperature of about 50° C.

First, clopidogrel hydrogensulfate is dissolved in 2-butanol. The solution may be heated to substantially dissolve the clopidogrel hydrogensulfate in the alcohol. Preferably, the solution is heated to about reflux.

After heating, the solution is cooled. In one embodiment, after cooling, the solvent is removed from the solution, preferably by evaporation under reduced pressure, to obtain a residue. An antisolvent is then added to the residue.

In another embodiment, after cooling the solution, the antisolvent is added to the solution without the removal of the solvent. The antisolvent is preferably added slowly, such as dropwise.

Preferably, the antisolvent is an ether. More preferably, each alkyl radical of the ether is independently selected from the group consisting of methyl, ethyl, propyl, isopropyl, butyl, 1-butyl, 2-butyl and t-butyl. Most preferably, the ether is diethyl ether or methyl-t-butylether.

After addition of the antisolvent, a precipitate forms. The solution or the suspension is optionally stirred from about a few hours to about several days. The precipitate is then separated. The precipitate may be separated by methods well known in the art, such as filtering.

After separation, the precipitate may optionally be washed with an organic solvent, such as an ether. The precipitate may then be dried. The pressure may be reduced or the temperature raised to accelerate the drying process. Preferably, the precipitate is dried in a vacuum oven at a temperature of about 40° C. to 70° C. for about 24 hours.

One skilled in the art may appreciate that the processes of the present invention may use clopidogrel free base rather than clopidogrel hydrogensulfate as a starting material. After preparing a solution of an alcohol and the free base, the free base may be treated with sulfuric acid to obtain the hydrogensulfate form. The solution is then preferably heated to reflux for a few hours. Preferably, the sulfuric acid used is about 20% to about 98% aqueous sulfuric acid, most preferably about 80% aqueous sulfuric acid. The molar equivalent of sulfuric acid to clopidogrel base used is preferably from about 0.66 equivalents to about 1.1 equivalents.

One skilled in the art would appreciate that the conditions and the yield may vary when starting with clopidogrel base rather than clopidogrel hydrogensulfate.

The yield and the conditions may further vary according to the molar ratio and the concentration of the sulfuric acid used. The examples of the present invention provide guidance to one skilled in the art regarding the optimal conditions.

One skilled in the art may also appreciate that the scope of the disclosure is not limited by the order of the additions in adding an antisolvent. For example, a mixture may be added to an antisolvent or vice versa, though an embodiment may prefer one over the other.

As a platelet inhibitor, clopidogrel is effective at suppressing the lethal effects of blood clotting. Platelet aggregation often occurs around damaged blood vessels. The blood vessels may only have minor fissures or plaques to induce platelet aggregation.

Platelet aggregation leads to the blockage of arteries, thus increasing the risk of primary and secondary strokes and heart attacks. By inhibiting platelet aggregation, clopidogrel hydrogensulfate reduces the risk of heart attacks and strokes. Clopidogrel is particularly effective in the secondary prevention of ischemic events, which are defined in the art as a decrease in the blood supply to a bodily organ, tissue, or part caused by constriction or obstruction of the blood vessels.

Pharmaceutical compositions of the present invention contain clopidogrel hydrogensulfate Forms III, IV, V, and the amorphous form, optionally in mixture with other Form (s) or amorphous clopidogrel and/or active ingredients. In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dixoide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, clopidogrel hydrogensulfate and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Capsules, tablets and lozenges, and other unit dosage forms preferably contain a base equivalent of about 75 mg, which is about 98 grams of clopidogrel hydrogensulfate Form III, IV, V, or the amorphous form. The unit dosage form as used herein refers to the amount of the various forms of clopidogrel contained in the vehicle of administration, such as a tablet or a capsule. In a preferred embodiment, the unit dosage in a tablet for oral administration contains a base equivalent of about 25 mg to 150 mg. Most preferably, it is about 75 mg base equivalent. One skilled in the art would appreciate that other unit dosages may be made as necessary in a routine fashion.

The instrumentation used for all the polymorphs was the same as that described for Form III.

For FTIR, KBr tablets were not used. In the prior art, Form II was characterized by FTIR using KBr tablets. As disclosed, Applicants performed FTIR by diffuse reflectance technique. Applicants also obtained a spectrum of Form II by using the diffuse reflectance technique, which depicted the same spectrum as that disclosed in the prior art.

EXAMPLES

Example 1

Preparation of Clopidogrel Hydrogensulfate Form II

Clopidogrel base (5.01 g, 1 eq.) was dissolved in methylethyl ketone (MEK) (39.5 mL). Eighty percent aqueous sulfuric acid (0.74 mL, 0.66 eq.) was added to the solution at 20° C. The reaction mixture was heated to reflux temperature for 2 hours. Then, the solution was cooled to room temperature and half of the amount of the solvent was evaporated under reduced pressure during which a precipitate was formed. The white solid was collected by filtration, washed with MEK (2×10 ml) and dried at 50° C. in a vacuum oven for 24 hours to obtain 3.55 g (54%) of clopidogrel hydrogensulfate crystal form II.

Example 2

Preparation of Clopidogrel Hydrogensulfate Form II

Clopidogrel base (4.27 g, 1 eq.) was dissolved in methylethyl ketone (MEK) (33.7 ml). Eighty percent aqueous sulfuric acid (1.03 ml, 1.1 eq.) was added to the solution at 20° C. The reaction mixture was heated to reflux temperature for 2 hours. Then, the solution was cooled to room temperature and stirred at this temperature for additional 67 hours during which a precipitate was formed. The white solid was collected by filtration, washed with MEK (2×10 mL) and dried at 50° C. in a vacuum oven for 24 hours to obtain 4.59 g (82%) of clopidogrel hydrogensulfate crystal form II.

Example 3

Preparation of Clopidogrel Hydrogensulfate Form II

Clopidogrel base (3.73 g, 1 eq.) was dissolved in dichloromethane (29.4 mL). Eighty percent aqueous sulfuric acid (0.55 ml, 0.66 eq.) was added to the solution at 20° C. The reaction mixture was heated to reflux temperature for 2 hours during which a precipitate was formed. Then, the solution was cooled to room temperature and half of the amount of the solvent was evaporated under reduced pressure. The white solid was collected by filtration, washed with dichloromethane (2×10 ml) and dried at 50° C. in a vacuum oven for 24 hours to obtain 1.42 g (30%) of clopidogrel hydrogensulfate crystal form II.

Example 4

Preparation of Clopidogrel Hydrogensulfate Form II

Clopidogrel base (4.37 g, 1 eq.) was dissolved in dichloromethane (34.5 mL). Eighty percent aqueous sulfuric acid (1.06 mL, 1.1 eq.) was added to the solution at 20° C. The reaction mixture was heated to reflux temperature for 2 hours during which a turbid solution was formed. Then, the solution was cooled to room temperature and stirred at this temperature for an additional 16 hours during which a massive precipitate was formed. The white solid was collected by filtration, washed with dichloromethane (2×10 ml) and dried at 50° C. in a vacuum oven for 24 hours to obtain 2.76 g (48%) of clopidogrel hydrogensulfate crystal form II.

Example 5

Preparation of Clopidogrel Hydrogensulfate Form II

Clopidogrel base (4.29 g, 1 eq.) was dissolved in toluene (33.8 mL). Eighty percent aqueous sulfuric acid (1.04 mL, 1.1 eq.) was added to the solution at 20° C. The reaction mixture was heated to reflux temperature for 3 hours. Then, the solution was cooled to room temperature and stirred at this temperature for an additional 16 hours during which a massive precipitate was formed. The white solid was collected by filtration, washed with toluene (2×10 ml) and dried at 50° C. in a vacuum oven for 24 hours to obtain 4.59 g (82%) of clopidogrel hydrogensulfate crystal form II.

Example 6

Preparation of Clopidogrel Hydrogensulfate Form II

Clopidogrel base (4.24 g, 1 eq.) was dissolved in chloroform (33.4 mL). Eighty percent aqueous sulfuric acid (0.62 mL, 0.66 eq.) was added to the solution at 20° C. The reaction mixture was heated to reflux temperature for 2 hours during which a precipitate was formed. Then, the solution was cooled to room temperature and half of the amount of the solvent was evaporated under reduced pressure. The white solid was collected by filtration, washed with chloroform (2×10 mL) and dried at 50° C. in a vacuum oven for 24 hours to obtain 3.14 g (56%) of clopidogrel hydrogensulfate crystal form II.

Example 7

Preparation of Clopidogrel Hydrogensulfate Form II

Clopidogrel base (4.37 g, 1 eq.) was dissolved in chloroform (34.5 mL). Eighty percent aqueous sulfuric acid (1.06 ml, 1.1 eq.) was added to the solution at 20° C. The reaction mixture was heated to reflux temperature for 2 hours during which a precipitate was formed. Then, the solution was cooled to room temperature and stirred at this temperature for an additional 16 hours during which a massive precipitate was formed. The white solid was collected by filtration, washed with chloroform (2×10 ml) and dried at 50° C. in a vacuum oven for 24 hours to obtain 5.01 g (88%) of Clopidogrel hydrogensulfate crystal form II.

Example 8

Preparation of Clopidogrel Hydrogensulfate Form II

Clopidogrel base (4.03 g, 1 eq.) was dissolved in ethyl acetate (31.8 mL). Eighty percent aqueous sulfuric acid (0.59 mL, 0.66 eq.) was added to the solution at 20° C. The reaction mixture was heated to reflux temperature for 3 hours during which a sticky precipitate was formed. Then, the solution was cooled to room temperature and stirred at this temperature for an additional 16 hours during which a massive precipitate was formed. The white solid was collected by filtration, washed with ethyl acetate (2×10 ml) and dried at 50° C. in a vacuum oven for 24 hours to obtain 2.59 g (49%) of clopidogrel hydrogensulfate crystal form II.

Example 9

Preparation of Clopidogrel Hydrogensulfate Form II

Clopidogrel base (5.31 g, 1 eq.) was dissolved in ethyl acetate (41.9 mL). Eighty percent aqueous sulfuric acid (1.29 mL, 1.1 eq.) was added to the solution at 20° C. The reaction mixture was heated to reflux temperature for 2 hours during which a massive precipitate was formed. Then, the solution was cooled to room temperature and stirred at this temperature for an additional 3 hours. The white solid was collected by filtration, washed with ethyl acetate (2×10 ml) and dried at 50° C. in a vacuum oven for 24 hours to obtain 4.60 g (66%) of clopidogrel hydrogensulfate crystal form II.

Example 10

Preparation of Clopidogrel Hydrogensulfate Form II

Clopidogrel base (4.39 g, 1 eq.) was dissolved in tert-butylmethyl ether (MTBE) (34.6 ml). Eighty percent aqueous sulfuric acid (0.64 ml, 0.66 eq.) was added to the solution at 20° C. The reaction mixture was heated to reflux temperature for 3 hours during which a sticky precipitate was formed. Then, the solution was cooled to room temperature and stirred at this temperature for an additional 2 hours. The obtained white solid was collected by filtration, washed with MTBE (2×10 mL) and dried at 50° C. in a vacuum oven for 24 hours to obtain 2.96 g (52%) of clopidogrel hydrogensulfate crystal form II.

Example 11

Preparation of Clopidogrel Hydrogensulfate Form II

Clopidogrel base (4.17 g, 1 eq.) was dissolved in 1,4-Dioxane (32.9 mL). Eighty percent aqueous sulfuric acid (0.61 ml, 0.66 eq.) was added to the solution at 20° C. The reaction mixture was heated to reflux temperature for 2 hours during which a massive precipitate was formed. Then, the solution was cooled to room temperature and stirred at this temperature for additional 2 hours. The white solid was collected by filtration, washed with 1,4-dioxane (2×10 mL) and dried at 50° C. in a vacuum oven for 24 hours to obtain 2.61 g (48%) of clopidogrel hydrogensulfate crystal form II.

Example 12

Preparation of Clopidogrel Hydrogensulfate Form II

Amorphous Clopidogrel hydrogensulfate (1 g) was dissolved in Acetonitrile (6 mL) at room temperature. The resulting solution was added to DEE (350 ml) drop wise and the obtained suspension was stirred at room temperature for 19 hours. The white solid was collected by filtration, washed with DEE (15 mL) and dried at 65° C. in a vacuum oven for 24 hours to obtain 0.71 g (71%) of clopidogrel hydrogensulfate crystal form Example 13

Preparation of Clopidogrel Hydrogensulfate Amorphous Form

Clopidogrel hydrogensulfate (3 grams) was dissolved in methanol (6 mL). Toluene (350 mL) was separately heated to reflux temperature. The methanolic solution of clopidogrel hydrogensulfate was added dropwise to the boiling toluene. The resulting solution was refluxed for an additional 20 minutes. The solution was cooled to room temperature and was stirred at this temperature for 16 hours. The solvent was evaporated under reduced pressure to dryness to obtain a creamy foam (1.26 grams, 42%), which characterization data showed to be the amorphous form.

Example 14

Preparation of Clopidogrel Hydrogensulfate Amorphous Form

Clopidogrel hydrogensulfate (2 grams) was dissolved in methanol (4 mL). The resulting solution was added dropwise to diethyl ether (350 mL). The suspension was stirred at RT for about forty five minutes. The solid was filtered and dried at about 50° C. in a vacuum oven for 24 hours to give 1.12 grams (56%) of clopidogrel hydrogensulfate, which characterization data showed to be the amorphous form.

Example 15

Preparation of Clopidogrel Hydrogensulfate Amorphous Form

Clopidogrel hydrogensulfate (1 gram) was dissolved in methanol (3 mL) at room temperature. The resulting solution was added drop wise to diethylether (DEE) (350 mL). The obtained mixture was stirred at room temperature for ½ hour. The solid was then filtered and dried at 50° C. in a vacuum oven for 16 hours to give 0.86 g (86%) of amorphous clopidogrel hydrogensulfate.

Example 16

Preparation of Clopidogrel Hydrogensulfate Amorphous Form

Clopidogrel base (3.42 g) was dissolved in acetone (27 mL). Aqueous sulfuric acid (20%, 4.57 mL) was added to the solution at 20° C. The reaction mixture was heated to reflux temperature for 2 hours. The solution was cooled to room temperature and stirred at this temperature for additional 1.5 hours. Then the solvent was evaporated to dryness under reduced pressure to obtain powder (3.59 g, 78%) which characterization data showed to be the amorphous form.

Example 17

Preparation of Clopidogrel Hydrogensulfate Amorphous Form

Clopidogrel base (2.88 g) was dissolved in acetone (23 mL). Aqueous sulfuric acid (20%, 2.56 mL) was added to the solution at 20° C. The reaction mixture was heated to reflux temperature for 2 hours. The solution was cooled to room temperature and stirred at this temperature for an additional 2 hours. Then the solvent was evaporated to dryness under reduced pressure to obtain powder (3.08 g, 82%) which characterization data showed to be the amorphous form.

Example 18

Preparation of Clopidogrel Hydrogensulfate Form I

Clopidogrel hydrogensulfate (2 grams) was dissolved in methanol (4 mL). The resulting solution was added to methyl t-butyl ether (300 mL) dropwise. The suspension was stirred at RT for 16 hours. The resulting precipitate was filtered and dried at 65° C. in a vacuum oven for 24 hours to obtain crystals (1.5 grams, 75%). Subsequent analysis confirmed that the crystals were clopidogrel hydrogensulfate Form I.

Example 19

Preparation of Clopidogrel Hydrogensulfate Form I

Clopidogrel hydrogensulfate (3 grams) was dissolved in absolute ethanol (9 mL) at reflux temperature to obtain a clear solution. The solution was then cooled to room temperature and the solvent was evaporated to dryness under reduced pressure to obtain oil. Then methy t-butyl ether or diethylether (28 mL) were added dropwise to the oily residue and the resulting mixture was stirred at room temperature for 24 hours. The white product was filtered and dried at 50° C. in a vacuum oven for 24 hours to give 2.6 grams (87%) of clopidogrel hydrogensulfate crystal Form I.

Example 20

Preparation of Clopidogrel Hydrogensulfate Form I

Clopidogrel hydrogensulfate (3 grams) was dissolved in methanol (4 mL) at reflux temperature to obtain a clear solution. The solution was then cooled to room temperature and the solvent was evaporated to dryness under reduced pressure to obtain oil. Then tert-butyl methylether or diethylether (30 mL) was added dropwise to the oily residue and the resulting mixture was stirred at room temperature for 16 hours. The white product was filtered and dried at 50° C. in a vacuum oven for 24 hours to give 2.65 grams (88%) of clopidogrel hydrogensulfate crystal Form I.

Example 21

Preparation of Clopidogrel Hydrogensulfate Form I and Amorphous Form

Clopidogrel base (3.85 g) was dissolved in absolute ethanol (30.4 mL). Eighty percent aqueous sulfuric acid (0.56 mL) was added to the solution. The reaction mixture was heated to reflux temperature for 2 hours. Then, the solution was cooled to room temperature and the solvent was evaporated to dryness under reduced pressure leaving a white foam. The foam was stirred in methyl t-butyl ether (MTBE) (70 ml) for 3 hours at room temperature. Approximately half of the MTBE was evaporated under reduced pressure and a solid was recovered by filtration. The solid was dried at 50° C. in a vacuum oven to obtain 2.82 g (56%) of a mixture of clopidogrel hydrogensulfate crystal form I and amorphous clopidogrel hydrogensulfate.

Example 22

Preparation of Clopidogrel Hydrogensulfate Form I

Clopidogrel hydrogensulfate (1 gram) was dissolved in methanol (3 mL) at room temperature. The resulting solution was added drop wise to diethylether (DEE) (350 mL). The obtained mixture was stirred at room temperature for 1 hour. The solid was then filtered and dried at 50° C. in a vacuum oven for 19.5 hours to give 0.76 g (76%) of clopidogrel hydrogensulfate crystal Form I.

Example 23

Preparation of Clopidogrel Hydrogensulfate Form I

Clopidogrel hydrogensulfate (1 gram) was dissolved in methanol (3 mL) at room temperature. The resulting solution was added drop wise to diethylether (DEE) (350 mL). The obtained mixture was stirred at room temperature for 5 hours. The solid was then filtered and dried at 50° C. in a vacuum oven for 14 hours to give 0.74 g (74%) of Clopidogrel hydrogensulfate crystal Form I.

Example 24

Preparation of Clopidogrel Hydrogensulfate Form I

Clopidogrel hydrogensulfate (1 gram) was dissolved in methanol (3 mL) at room temperature. The resulting solution was added drop wise to diethylether (DEE) (350 mL). The obtained mixture was stirred at room temperature for 8 hours. The solid was then filtered and dried at 50° C. in a vacuum oven for 13 hours to give 0.78 g (78%) of Clopidogrel hydrogensulfate crystal Form I.

Example 25

Preparation of Clopidogrel Hydrogensulfate Form I

Clopidogrel hydrogensulfate (1 gram) was dissolved in methanol (3 mL) at room temperature. The resulting solution was added drop wise to diethylether (DEE) (350 mL). The obtained mixture was stirred at room temperature for 19.5 hours. The solid was then filtered and dried at 50° C. in a vacuum oven for 23 hours to give 0.74 g (74%) of clopidogrel hydrogensulfate crystal Form I.

Example 26

Preparation of Clopidogrel Crystal Form III

A suspension of clopidogrel hydrogensulfate (3 grams) in 1-butanol (5 mL) was heated to reflux temperature for 30 minutes to obtain a clear solution. The solution was cooled to room temperature (RT) and the solvent was evaporated under reduced pressure to obtain an oily residue. Diethyl ether (30 mL) was added to the residue. The resulting mixture was stirred at room temperature for 24–48 hours. A white product precipitated from the mixture, and was then filtered, and washed with diethyl ether (2×10 mL). The white product was dried at 65° C. in a vacuum oven for 24 hours to give 2.91 grams of crystalline clopidogrel hydrogensulfate (97%), which was identified as Form III by PXRD.

Example 27

Preparation of Clopidogrel Crystal Form III

Clopidogrel base (4.28 g) was dissolved in 1-butanol (16.9 ml). Eighty percent aqueous sulfuric acid (0.63 ml) was added to the solution at 20° C. The reaction mixture was heated to reflux temperature for 2 hours. Then, the solution was cooled to room temperature and the solvent was evaporated to dryness under reduced pressure leaving yellow oil. The oil was stirred in methyl t-butyl ether (MTBE) (125 ml) for 96 hours at room temperature to obtain a precipitate. The solid was collected by filtration, washed with MTBE (2×10 ml) and dried at 50° C. in a vacuum oven for 24 hours to obtain 3.33 g (60%) of clopidogrel hydrogensulfate crystal Form Example 28

Preparation of Clopidogrel Crystal Form III

Clopidogrel hydrogensulfate crystal form I (1 g) was dissolved in 1-butanol (5 mL) at reflux temperature. When a clear solution was obtained, the solution was cooled to room temperature and the solvent was evaporated to dryness under reduced pressure to obtain an oily residue. Then Diethyl ether (DEE) (7 mL) was added to the residue and the resulting mixture was stirred at room temperature for 24 hours during which a precipitate was formed. The white solid was collected by filtration, washed with DEE (25 mL) and dried at 60° C. in a vacuum oven for 20 hours to obtain 0.86 g (86%) of clopidogrel hydrogensulfate crystal form III.

Example 29

Preparation of Clopidogrel Hydrogensulfate Form IV

Clopidogrel hydrogensulfate (3 grams) was dissolved in isopropanol (IPA) (32 mL (~11 vol.)) at reflux temperature. The resulting solution was cooled to room temperature and stirred at this temperature for 1 hour. The solid was then filtered and dried at 50° C. in a vacuum oven for 16 hours to give 1.66 g (55%) of clopidogrel hydrogensulfate crystal Form IV.

Remark: The volume of the solvent can be increased up to 21 volumes/1 g of clopidogrel hydrogensulfate.

Example 30

Preparation of Clopidogrel Hydrogensulfate Form IV

Clopidogrel hydrogensulfate (3 grams) was dissolved in isopropanol (IPA) (60 ml (20 vol.)) at reflux temperature. The resulting solution was cooled to room temperature and the solvent was evaporated to dryness under reduced pressure to give 2.0 g (67%) of clopidogrel hydrogensulfate crystal form IV.

Example 31

Preparation of Clopidogrel Hydrogensulfate Form IV

Clopidogrel base (2.96 g) was dissolved in isopropanol (45 mL). Aqueous sulfuric acid (98%, 0.50 ml) was added to the solution at 20° C. The reaction mixture was heated to reflux temperature for 2 hours. Then, the solution was cooled to room temperature and stirred at this temperature for an additional 2 hours to obtain a white precipitate. The solid was collected by filtration, washed with isopropanol (2×10 ml) and dried at 50° C. in a vacuum oven for 28 hours to obtain 2.78 g (71%) of clopidogrel hydrogensulfate crystal Form IV.

Example 32

Preparation of Clopidogrel Hydrogensulfate Form IV

Clopidogrel base (2.91 g) was dissolved in isopropanol (IPA) (44 ml). Ninety eight percent aqueous sulfuric acid (0.32 ml) was added to the solution at 20° C. The reaction mixture was heated to reflux temperature for 2 hours. Then, the solution was cooled to room temperature and stirred at this temperature for an additional 2 hours to obtain a white precipitate. The solid was collected by filtration, washed with IPA (2×10 ml) and dried at 50° C. in a vacuum oven for 26 hours to obtain 3.04 g (80%) of clopidogrel hydrogensulfate crystal Form IV.

Example 33

Preparation of Clopidogrel Hydrogensulfate Form IV

Clopidogrel base (2.93 g) was dissolved in isopropanol (45 ml). Sixty percent aqueous sulfuric acid (0.99 mL) was added to the solution at 20° C. The reaction mixture was heated to reflux temperature for 2 hours. Then, the solution was cooled to room temperature and stirred at this temperature for an additional 2.5 hours to obtain a white precipitate. The solid was collected by filtration, washed with isopropanol (2×10 ml) and dried at 50° C. in a vacuum oven for 15 hours to obtain 2.22 g (58%) of clopidogrel hydrogensulfate crystal Form IV.

Example 34

Preparation of Clopidogrel Hydrogensulfate Form IV

Clopidogrel base (2.98 g) was dissolved in isopropanol (45 mL). Sixty percent aqueous sulfuric acid (0.67 ml) was added to the solution at 20° C. The reaction mixture was heated to reflux temperature for 2 hours. Then, the solution was cooled to room temperature and stirred at this temperature for additional 2 hours to obtain a white precipitate. The solid was collected by filtration, washed with IPA (2×10 ml) and dried at 50° C. in a vacuum oven for 15 hours to obtain 0.93 g (24%) of clopidogrel hydrogensulfate crystal Form IV.

Example 35

Preparation of Clopidogrel Hydrogensulfate Form IV

Clopidogrel base (2.85 g) was dissolved in isopropanol (43 mL). Forty percent aqueous sulfuric acid (1.67 mL) was added to the solution at 20° C. The reaction mixture was heated to reflux temperature for 2 hours. Then, the solution was cooled to room temperature and stirred at this temperature for additional 3.5 hours to obtain a white precipitate. The solid was collected by filtration, washed with IPA (2×10 ml) and dried at 50° C. in a vacuum oven for 14.5 hours to obtain 1.47 g (40%) of clopidogrel hydrogensulfate crystal Form IV.

Example 36

Preparation of Clopidogrel Hydrogensulfate Form IV

Clopidogrel base (2.95 g) was dissolved in isopropanol (45 ml). Forty percent aqueous sulfuric acid (1.15 mL) was added to the solution at 20° C. The reaction mixture was heated to reflux temperature for 2 hours. Then, the solution was cooled to room temperature and stirred at this temperature for an additional 3.5 hours to obtain a white precipitate. The solid was collected by filtration, washed with IPA (2×10 mL) and dried at 50° C. in a vacuum oven for 14.5 hours to obtain 0.49 g (13%) of clopidogrel hydrogensulfate crystal Form IV.

Example 37

Preparation of Clopidogrel Hydrogensulfate Form IV

Clopidogrel base (2.89 g) was dissolved in isopropanol (44 mL). Eighty percent aqueous sulfuric acid (0.42 mL) was added to the solution at 20° C. The reaction mixture was heated to reflux temperature for 2 hours. The solution was cooled to room temperature and stirred at this temperature for an additional 5 hours. Then half of the solvent was removed by evaporation under reduced pressure and the resulting solution was stirred at room temperature for 45 minutes to obtain a white precipitate. The solid was collected by filtration, washed with IPA (3×10 ml) and dried at 50° C. in a vacuum oven for 15 hours to obtain 1.24 g (33%) of clopidogrel hydrogensulfate crystal Form IV.

Example 38

Preparation of Clopidogrel Hydrogensulfate Form IV

Clopidogrel base (2.96 g) was dissolved in isopropanol (IPA) (45 mL). Eighty percent aqueous sulfuric acid (0.65 mL) was added to the solution at 20° C. The reaction mixture was heated to reflux temperature for 2 hours. Then, the solution was cooled to room temperature and stirred at this temperature for an additional 1.5 hours to obtain a white precipitate. The solid was collected by filtration, washed with IPA (2×10 ml) and dried at 50° C. in a vacuum oven for 15 hours to obtain 3.24 g (84%) of clopidogrel hydrogensulfate crystal Form IV.

Example 39

Preparation of Clopidogrel Hydrogen Sulfate Form V

Clopidogrel hydrogensulfate (3 grams) was dissolved in 2-butanol (9 mL) at reflux temperature. The resulting solution was cooled to room temperature and methyl tert-butylether (MTBE) (40 mL) was added drop wise. The obtained mixture was stirred at room temperature for 72 hours. The solid was then filtered and dried at 50° C. in a vacuum oven for 24 hours to give 3.15 g of clopidogrel hydrogensulfate crystal Form V.

Example 40

Preparation of Clopidogrel Hydrogensulfate Form V

Clopidogrel hydrogensulfate (3 grams) was dissolved in 2-butanol (8 mL) at reflux temperature. The resulting solution was cooled to room temperature and the solvent was evaporated to dryness under reduced pressure. Then diethylether (DEE) (26 mL) was added drop wise and the obtained mixture was stirred at room temperature for 24 hours. The solid was then filtered and dried at 50° C. in a vacuum oven for 24 hours to give 3.08 g of clopidogrel hydrogensulfate crystal Form V.

Example 41

Preparation of Clopidogrel Hydrogensulfate Form V

Clopidogrel hydrogensulfate (3 grams) was dissolved in 2-butanol (14 mL) at reflux temperature. The resulting solution was cooled to room temperature. Then MTBE (35 mL) was added drop wise and the obtained mixture was stirred at room temperature for 16 hours. Additional MTBE (11 mL) was added and the suspension was stirred at room temperature for additional 2 hours. The solid was filtered, washed with MTBE (25 mL) and dried at 65° C. in a vacuum oven for 24 hours to give 2.95 g (98%) of clopidogrel hydrogensulfate crystal Form V.

Example 42

Preparation of Clopidogrel Hydrogensulfate Form V

Clopidogrel base (2.98 g) was dissolved in 2-butanol (23 mL). Ninety eight percent aqueous sulfuric acid (0.50 mL) was added to the solution at 20° C. The reaction mixture was heated to reflux temperature for 2 hours. The solution was cooled to room temperature and stirred at this temperature for an additional 3 hours. Then the solvent was evaporated to dryness under reduced pressure to obtain an oil. Then tert-Butyl methyl ether (MTBE) (44 mL) was added to the oily residue and the resulting mixture was stirred at room temperature for 16 hours. The precipitate was collected by filtration, washed with MTBE (2×10 ml) and dried at 50° C. in a vacuum oven for 22.5 hours to obtain 3.38 g (87%) of clopidogrel hydrogensulfate crystal Form V.

Example 43

Preparation of Clopidogrel Hydrogensulfate Form V

Clopidogrel base (2.94 g) was dissolved in 2-butanol (23 ml). Ninety eight percent aqueous sulfuric acid (0.43 ml) was added to the solution at 20° C. The reaction mixture was heated to reflux temperature for 2 hours. The solution was cooled to room temperature and stirred at this temperature for additional 1.5 hours. Then the solvent was evaporated to dryness under reduced pressure to obtain oil. Then diethyl ether (DEE) (40 ml) was added to the oily residue and the resulting mixture was stirred at room temperature for 16 hours. The precipitate was collected by filtration, washed with DEE (2×10 mL) and dried at 50° C. in a vacuum oven for 19 hours to obtain 2.11 g (55%) of clopidogrel hydrogensulfate crystal Form V.

Example 44

Preparation of Clopidogrel Hydrogensulfate Form VI

Clopidogrel base (2.86 g, 1 eq.) was dissolved in 1-Propanol (22.6 mL). Eighty percent aqueous sulfuric acid (0.59 mL, 0.66 eq.) was added to the solution at 20° C. The reaction mixture was heated to reflux temperature for 2 hours. Then, the solution was cooled to room temperature and stirred at this temperature for additional 16 hours. The solvent was evaporated to dryness under reduced pressure to obtain an oily residue. To the residue, MTBE (50 mL) was added and the resulting mixture was stirred at room temperature for 24 hours during which a massive precipitate was formed. The white solid was collected by filtration, washed with MTBE (2×10 mL) and dried at 50° C. in a vacuum oven for 30 hours to obtain 2.58 g (69%) of clopidogrel hydrogensulfate crystal form VI.

Having thus described the invention with reference to particular preferred embodiments and illustrated it with examples, those in the art may appreciate modifications to the invention as described and illustrated that do not depart from the spirit and scope of the invention as disclosed in the specification.

What is claimed is:

1. Clopidogrel hydrogensulfate Form III.
2. Clopidogrel hydrogensulfate having a powder X-ray diffraction pattern with peaks at about 8.1, 8.7, 14.3, 15.4, 20.1, 22.3, 22.5, 23.5, and 24.1±0.2 degrees two-theta.
3. The clopidogrel hydrogensulfate of claim 2 having a powder X-ray diffraction pattern as substantially depicted in FIG. 1.
4. Clopidogrel hydrogensulfate characterized by a differential scanning calorimetric thermogram having an endothermic peak at about 105° C.
5. Clopidogrel hydrogensulfate having a FTIR spectrum with peaks at about 581, 707, 755, 971, 1057, 1196, 1252, 1436, 1476, 1748, 2590, 2670 and 2963 cm.
6. The clopidogrel hydrogensulfate of claim 5 further characterized by FTIR spectrum peaks at about 886, 1323, 1594 $cm^{-1}$.
7. The clopidogrel hydrogensulfate of claim 6 having a FTIR spectrum as substantially depicted in FIG. 3.
8. A process for preparing clopidogrel hydrogensulfate Form III comprising the steps of:
   a) preparing a solution of clopidogrel hydrogensulfate in 1-butanol;
   b) removing the 1-butanol from the solution to obtain a residue;
   c) adding in any order an antisolvent to the residue to cause formation of a precipitate;
   d) separating the precipitate; and
   e) drying the precipitate.
9. The process of claim 8, wherein the 1-butanol is removed by evaporation.
10. The process of claim 8, wherein the solution is prepared by mixing clopidogrel base, sulfuric acid and 1-butanol.
11. The process of claim 8, wherein the clopidogrel hydrogensulfate Form III is obtained in a yield of at least about 97%.
12. The process of claim 8, wherein the antisolvent is an ether.
13. The process of claim 12, wherein each alkyl radical of the ether is independently selected from the group consisting of methyl, ethyl, propyl, isopropyl, butyl, 1-butyl, 2-butyl and t-butyl.
14. The process of claim 13, wherein the ether is diethyl ether.
15. Amorphous form of clopidogrel hydrogensulfate.
16. Clopidogrel hydrogensulfate having a PXRD pattern as substantially depicted in FIG. 4.
17. Clopidogrel hydrogensulfate having a FTIR spectrum with peaks at about 583, 723, 762, 846, 1040, 1167, 1223, 1438, 1478, 1638, 1752, 2585 and 2960 $cm^{-1}$.
18. The clopidogrel hydrogensulfate of claim 17 having a FTIR spectrum as substantially depicted in FIG. 5.
19. A process for preparing amorphous form of clopidogrel hydrogensulfate
   comprising the steps of:
   a) preparing a solution of clopidogrel hydrogensulfate in an alcohol selected from the group consisting of methanol and ethanol;
   b) adding in any order the solution to an antisolvent to cause formation of a precipitate; and
   c) separating the precipitate.
20. The process of claim 19, wherein preparing the solution comprises mixing clopidogrel base, sulfuric acid and an alcohol selected from the group consisting of methanol and ethanol.

21. The process of claim 19, wherein the anti-solvent is an ether.

22. The process of claim 21, wherein each alkyl radical of the ether is independently selected from the group consisting of methyl, ethyl, propyl, isopropyl, butyl, 1-butyl, 2-butyl and t-butyl.

23. The process of claim 22, wherein the ether is selected from the group consisting of diethyl ether and t-butyl methyl ether.

24. The process of claim 19, wherein a portion of the precipitate is converted into Form I before separation.

25. The process of claim 19, further comprising a drying step.

26. A process for preparing amorphous form of clopidogrel hydrogensulfate
   comprising the steps of:
   a) preparing a solution of clopidogrel hydrogensulfate in an alcohol selected from the group consisting of methanol and ethanol;
   b) removing the alcohol from the solution to obtain a residue;
   c) adding in any order an antisolvent to the residue to cause formation of a precipitate; and
   d) separating the precipitate.

27. The process of claim 26, wherein the alcohol is removed by evaporation.

28. The process of claim 26, wherein preparing the solution comprises mixing clopidogrel base, sulfuric acid and an alcohol selected from the group consisting of methanol and ethanol.

29. The process of claim 26, wherein the anti-solvent is an ether.

30. The process of claim 29, wherein each alkyl radical of the ether is independently selected from the group consisting of methyl, ethyl, propyl, isopropyl, butyl, 1-butyl, 2-butyl and t-butyl.

31. The process of claim 30, wherein the ether is selected from the group consisting of diethyl ether and t-butyl methyl ether.

32. The process of claim 26, wherein a portion of the precipitate is converted into Form I before separating the ether.

33. The process of claim 26, further comprising a drying step.

34. A process for preparing amorphous form of clopidogrel hydrogensulfate comprising the steps of:
   a) preparing a solution of clopidogrel hydrogensulfate in an alcohol selected from the group consisting of methanol and ethanol;
   b) adding in any order the solution to an antisolvent; and
   c) removing the alcohol and the antisolvent.

35. The process of claim 34, wherein preparing the solution comprises mixing clopidogrel base, sulfuric acid and an alcohol selected from the group consisting of methanol and ethanol.

36. The process of claim 34, wherein the alcohol and the antisolvent are removed by evaporation.

37. The process of claim 34, wherein the antisolvent is a one ring aromatic compound.

38. The process of claim 37, wherein the one ring aromatic compound is selected from the group consisting of xylene, toluene and benzene.

39. The process of claim 38, wherein the one ring aromatic compound is toluene.

40. The process of claim 34, further comprising concentrating the solution before addition to the antisolvent.

41. A process for preparing amorphous form of clopidogrel hydrogensulfate comprising preparing a solution of clopidogrel hydrogensulfate in acetone, and removing the acetone.

42. The process of claim 41, wherein the acetone is removed by evaporation.

43. The process of claim 41, wherein preparing the solution comprises mixing clopidogrel base, sulfuric acid and acetone.

44. A process for preparing clopidogrel hydrogensulfate Form I comprising contacting amorphous clopidogrel hydrogensulfate with an ether, and separating clopidogrel Form I.

45. The process of claim 44, wherein each alkyl radical of the ether is independently selected from the group consisting of methyl, ethyl, propyl, isopropyl, butyl, 1-butyl, 2-butyl and t-butyl.

46. The process of claim 45, wherein the ether is selected from the group consisting of diethyl ether and methyl t-butyl ether.

47. The process of claim 44, wherein the amorphous clopidogrel hydrogensulfate is suspended in the ether.

48. The process of claim 47, wherein the clopidogrel hydrogensulfate is suspended in ether for more than about 1 hour.

49. The process of claim 48, wherein the amorphous clopidogrel hydrogensulfate is suspended in ether for more than about 4 hours to obtain substantially Form I.

50. Clopidogrel hydrogensulfate Form IV.

51. Clopidogrel hydrogensulfate characterized by a PXRD pattern with peaks at about 22.0, 25.9, 26.9, 27.4, 28.1, 28.6 and 28.9±0.2 degrees two theta.

52. The clopidogrel hydrogensulfate of claim 51, further characterized by PXRD peaks at about 11.0, 12.5, 13.3, 14.0, 17.6, 18.2, 18.8, 20.5, 22.9, 24.1±0.2 degrees two theta.

53. The clopidogrel hydrogensulfate of claim 52, characterized by a PXRD spectrum as substantially depicted in FIG. 6.

54. Clopidogrel hydrogensulfate characterized by a DTG thermogram with an endothermic peak at about 160–170° C.

55. Clopidogrel hydrogensulfate characterized by a FTIR spectrum with peaks at about 618, 769, 842, 893, 935, 974, 1038, 1116, 1370, 1384 cm$^{-1}$.

56. The clopidogrel hydrogensulfate of claim 55, characterized by a FTIR spectrum as substantially depicted in FIG. 8.

57. A process for preparing clopidogrel hydrogensulfate Form IV comprising forming a precipitate from a solution of clopidogrel hydrogensulfate and isopropanol, and separating the precipitate.

58. The process of claim 57, wherein a precipitate is formed by heating the solution followed by cooling the solution.

59. The process of claim 57, wherein the precipitate is separated by the techniques consisting of filtering, decanting and centrifugation.

60. The process of claim 57, further comprising a step of drying the precipitate.

61. The process of claim 57, wherein a precipitate is formed by removing the isopropanol.

62. The process of claim 61, wherein the precipitate is separated from the isopropanol and optionally dried by further removal of the isopropanol.

63. The process of claim 61, wherein the isopropanol is removed by evaporation.

64. Clopidogrel hydrogensulfate Form V.

65. Clopidogrel hydrogensulfate characterized by a PXRD diffraction pattern with peaks at about 25.5, 26.6, 27.8 and 28.5±0.2 degrees two theta.

66. The clopidogrel hydrogensulfate of claim 65, further characterized by PXRD peaks at about 11.0, 12.4, 13.1, 13.8, 15.2, 17.5, 18.1±0.2 degrees two theta.

67. The clopidogrel hydrogensulfate of claim 66, characterized by a PXRD pattern as substantially depicted in FIG. 9.

68. Clopidogrel hydrogensulfate characterized by a DSC profile with an endothermic peak at about 126–132° C.

69. Clopidogrel hydrogensulfate characterized by a FTIR spectrum with peaks at about 623, 743, 802, 817, 843, 963, 972, 1028 and 1374 $cm^{-1}$.

70. The clopidogrel hydrogensulfate of claim 69, characterized by a FTIR spectrum as substantially depicted in FIG. 11.

71. A process for preparing clopidogrel Form V comprising the steps of:
 a) preparing a solution of clopidogrel hydrogensulfate in 2-butanol;
 b) adding in any order an antisolvent to the solution to cause formation of a precipitate; and
 c) separating the precipitate.

72. The process of claim 71, further comprising a step of drying the precipitate.

73. The process of claim 71, wherein the antisolvent is an ether.

74. The process of claim 73, wherein each alkyl radical of the ether is independently selected from the group consisting of methyl, ethyl, propyl, isopropyl, butyl, 1-butyl, 2-butyl and t-butyl.

75. The process of claim 74, wherein the ether is selected from the group consisting of diethyl ether and methyl-t-butylether.

76. The process of claim 71, wherein preparing the solution comprises mixing clopidogrel base, sulfuric acid and 2-butanol.

77. A process for preparing clopidogrel Form V comprising the steps of
 a) preparing a solution of clopidogrel hydrogensulfate in 2-butanol;
 b) removing the 2-butanol from the solution to obtain a residue;
 c) adding in any order an antisolvent to the residue to cause formation of a precipitate; and
 d) separating the precipitate.

78. The process of claim 77, wherein the butanol is removed by evaporation.

79. The process of claim 77, wherein the antisolvent is an ether.

80. The process of claim 79, wherein each alkyl radical of the ether is independently selected from the group consisting of methyl, ethyl, propyl, isopropyl, butyl, 1-butyl, 2-butyl and t-butyl.

81. The process of claim 80, wherein the ether is selected from the group consisting of diethyl ether and methyl t-butylether.

82. The process of claim 77, wherein preparing the solution comprises mixing clopidogrel base, sulfuric acid and 2-butanol.

83. A pharmaceutical composition comprising clopidogrel hydrogensulfate selected from the group consisting of clopidogrel hydrogensulfate Form III, Form IV, Form V and amorphous form, and a pharmaceutically acceptable excipient.

84. The pharmaceutical composition of claim 83, wherein the pharmaceutical composition is mixed with one or more forms of clopidogrel hydrogen sulfate.

85. A pharmaceutical dosage form comprising the pharmaceutical composition of claim 84.

86. The pharmaceutical dosage form of claim 85, wherein the dosage form is a capsule or tablet.

87. The pharmaceutical dosage form of claim 86, wherein the dosage form is a tablet.

88. The pharmaceutical dosage form of claim 85, containing a unit dosage of about 25 to 175 mg base equivalent of clopidogrel hydrogensulfate.

89. The pharmaceutical dosage form of claim 88, containing a unit dosage of about 75 mg base equivalent clopidogrel hydrogensulfate.

90. The pharmaceutical dosage form of claim 88, containing a unit dosage of about 98 mg of clopidogrel hydrogen sulfate.

* * * * *

UNITED STATES PATENT AND TRADEMARK OFFICE
CERTIFICATE OF CORRECTION

PATENT NO. : 6,767,913 B2
DATED : July 27, 2004
INVENTOR(S) : Lifshitz et al.

It is certified that error appears in the above-identified patent and that said Letters Patent is hereby corrected as shown below:

Column 3,
Line 40, change "dichlormethane" to -- dichloromethane --

Column 4,
Line 4, change "Form III" to -- Form III which --

Column 6,
Line 10, change "Stare" to -- Star $^e$ --
Line 60, change "staring" to -- starting --

Column 11,
Line 53, change "pregelitinized" to -- pregelatinized --

Column 12,
Lines 25, 27 and 30, change "dye" to -- die --
Line 64, change "alginic acid bentonite" to -- alginic acid, bentonite --
Line 66, change "geltin guar gum" to -- geltin, guar gum --

Column 13,
Line 13, change "guconic" to -- gluconic --
Line 14, change "guconate" to -- gluconate --
Line 34, cahnge "losenges" to -- lozenges --

Column 17,
Line 6, change "form" to -- form II --

Column 18,
Line 26, change "methyl-t-butyl ether" to -- methyl t-butyl ether --

UNITED STATES PATENT AND TRADEMARK OFFICE
CERTIFICATE OF CORRECTION

PATENT NO. : 6,767,913 B2
DATED : July 27, 2004
INVENTOR(S) : Lifshitz et al.

It is certified that error appears in the above-identified patent and that said Letters Patent is hereby corrected as shown below:

Column 20,
Line 5, change "Form" to -- Form III --

Column 24,
Line 14, change "cm" to -- $cm^{-1}$ --

Signed and Sealed this

Second Day of August, 2005

JON W. DUDAS
*Director of the United States Patent and Trademark Office*